(12) United States Patent
Maxfield

(10) Patent No.: US 11,071,822 B2
(45) Date of Patent: Jul. 27, 2021

(54) MEDICAMENT DELIVERY DEVICE WITH ROTATOR RETAINING THE PLUNGER ROD

(71) Applicant: Carebay Europe Ltd., Swatar (MT)

(72) Inventor: Brian Maxfield, Boca Raton, FL (US)

(73) Assignee: SHL MEDICAL AG, Zug (CH)

( * ) Notice: Subject to any disclaimer, the term of this patent is extended or adjusted under 35 U.S.C. 154(b) by 277 days.

(21) Appl. No.: 15/309,082

(22) PCT Filed: Apr. 23, 2015

(86) PCT No.: PCT/EP2015/058779
§ 371 (c)(1),
(2) Date: Nov. 4, 2016

(87) PCT Pub. No.: WO2015/169608
PCT Pub. Date: Nov. 12, 2015

(65) Prior Publication Data
US 2017/0080153 A1 Mar. 23, 2017

(30) Foreign Application Priority Data
May 6, 2014 (SE) .................................. 1450532-5

(51) Int. Cl.
*A61M 5/20* (2006.01)
*A61M 5/32* (2006.01)
(Continued)

(52) U.S. Cl.
CPC ...... *A61M 5/2033* (2013.01); *A61M 5/31576* (2013.01); *A61M 5/3202* (2013.01);
(Continued)

(58) Field of Classification Search
CPC ............ A61M 5/2033; A61M 5/31576; A61M 5/31578; A61M 5/3158; A61M 5/31581;
(Continued)

(56) References Cited

U.S. PATENT DOCUMENTS 5,318,544 A * 6/1994 Drypen ............... A61M 5/3155
604/210
5,378,240 A * 1/1995 Curie .................. A61M 5/3234
604/110
(Continued)

FOREIGN PATENT DOCUMENTS

CH    WO 2013016832 A1 *  2/2013  .......... A61M 5/2033
DE    102006038103 A1    2/2008
(Continued)

OTHER PUBLICATIONS

Patent Translate: Translation of WO 2013/016832 A1, Jan. 17, 2018.*
(Continued)

*Primary Examiner* — Nilay J Shah
(74) *Attorney, Agent, or Firm* — McDonnell Boehnen Hulbert & Berghoff LLP

(57) ABSTRACT

A medicament delivery device extends along a longitudinal axis and includes: a generally tubular elongated housing having a proximal and a distal end, where the generally tubular elongated housing is arranged to accommodate a medicament container; a drive unit comprising a drive element and plunger rod operably arranged to act on the medicament container; a tubular element rotatable rotatably arranged in relation to the housing and operably arranged to the plunger rod, where the plunger rod includes at least one holding member and where the tubular element includes at least one arm extending generally transversal to the longitudinal axis of the device, wherein the at least one arm is arranged to engage the at least one holding member on plunger rod to releasable hold the drive unit in an energy accumulated state.

17 Claims, 20 Drawing Sheets

(51) Int. Cl.
*A61M 5/315* (2006.01)
*A61M 5/50* (2006.01)
*A61M 5/24* (2006.01)

(52) U.S. Cl.
CPC ............ *A61M 5/326* (2013.01); *A61M 5/24* (2013.01); *A61M 5/50* (2013.01); *A61M 2005/2013* (2013.01); *A61M 2005/2073* (2013.01); *A61M 2005/3247* (2013.01)

(58) Field of Classification Search
CPC ............ A61M 5/31586; A61M 5/3202; A61M 5/322; A61M 5/3234; A61M 5/3243; A61M 5/3257; A61M 5/326; A61M 5/24; A61M 2005/3267; A61M 2005/2013
See application file for complete search history.

(56) References Cited

U.S. PATENT DOCUMENTS

| | | | |
|---|---|---|---|
| 7,717,877 | B2 | 5/2010 | Lavi et al. |
| 8,496,619 | B2 | 7/2013 | Kramer et al. |
| 8,740,871 | B2 | 6/2014 | Lawlis et al. |
| 9,022,994 | B2 | 5/2015 | Moser et al. |
| 2004/0236285 | A1* | 11/2004 | Fisher ............... A61M 5/3158 604/207 |
| 2005/0101919 | A1 | 5/2005 | Brunnberg |
| 2008/0262436 | A1 | 10/2008 | Olson |
| 2012/0235136 | A1 | 9/2012 | Ogawa et al. |
| 2013/0041323 | A1* | 2/2013 | Daniel ............... A61M 5/2033 604/189 |
| 2013/0218094 | A1 | 8/2013 | Hommann et al. |

FOREIGN PATENT DOCUMENTS

| | | |
|---|---|---|
| JP | 2008-521482 A | 6/2008 |
| JP | 2013-530024 A | 7/2013 |
| WO | 2006057604 A1 | 6/2006 |
| WO | 2011139212 A1 | 11/2011 |
| WO | 2012003516 A2 | 1/2012 |
| WO | 2012003919 A2 | 1/2012 |
| WO | 2013016832 A1 | 2/2013 |

OTHER PUBLICATIONS

English Translation of Abstract of PCT Patent Application No. WO 2013/016832 dated Jan. 17, 2019.
Search Report issued in Taiwanese Patent Application No. 104113913 dated Mar. 1, 2016.
Examination Report issued in Australian Patent Application No. 2015257935 dated Dec. 6, 2016.
English Translation of Office Action issued in Japanese Patent Application No. 2016-566647 dated Oct. 26, 2017.

* cited by examiner

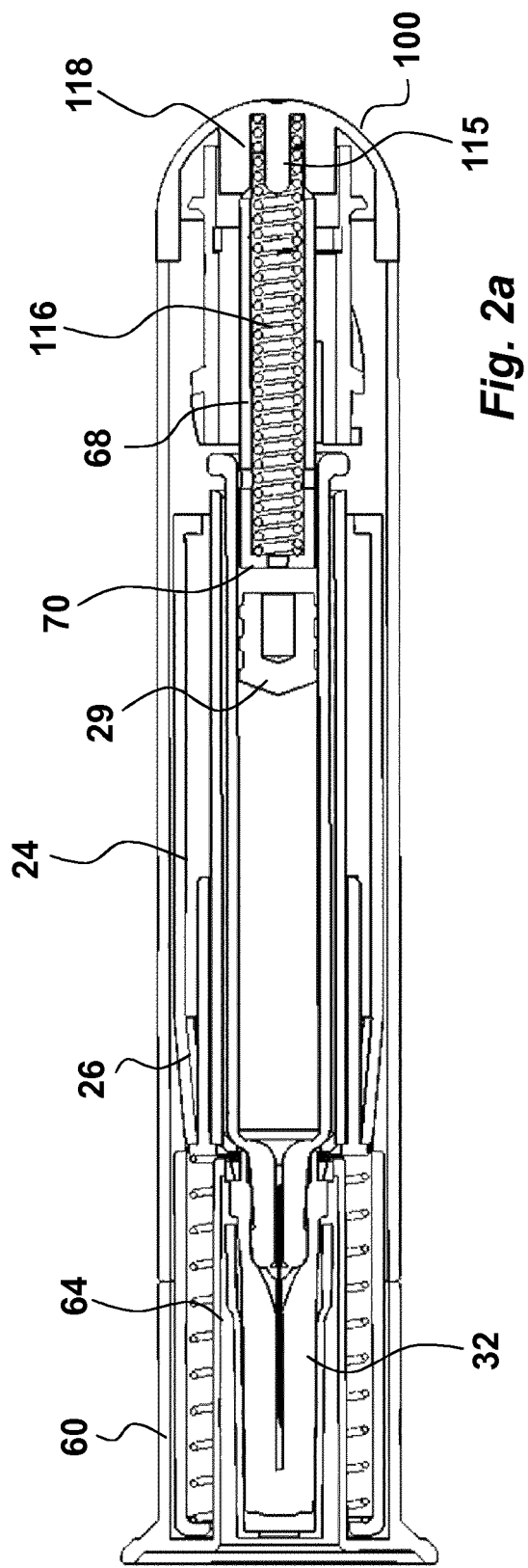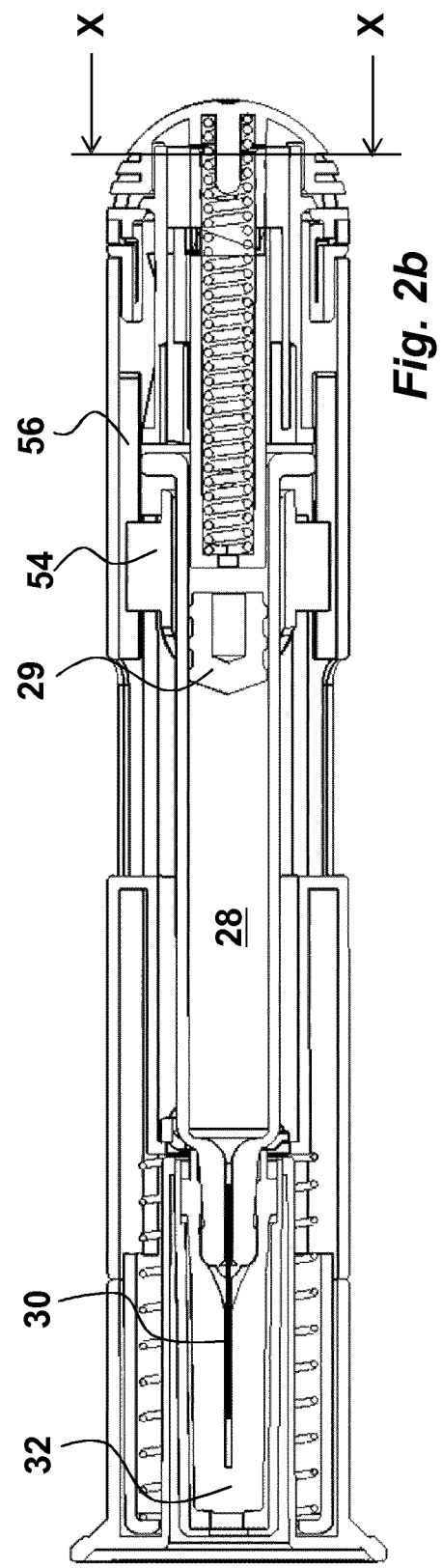
Fig. 2a
Fig. 2b

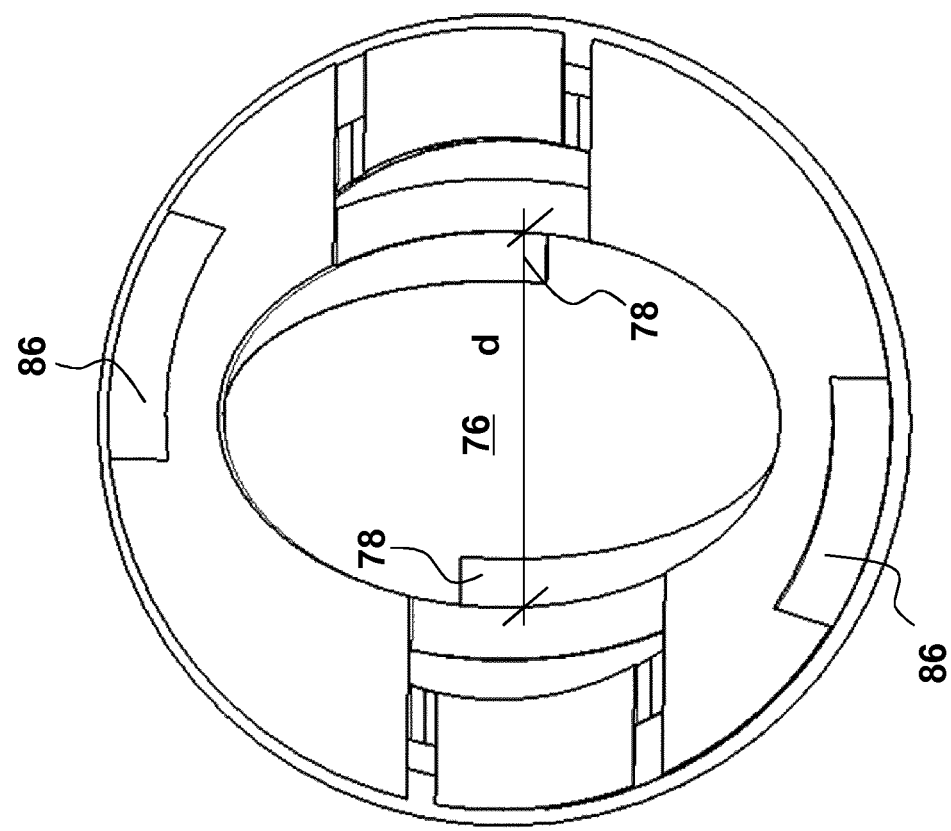
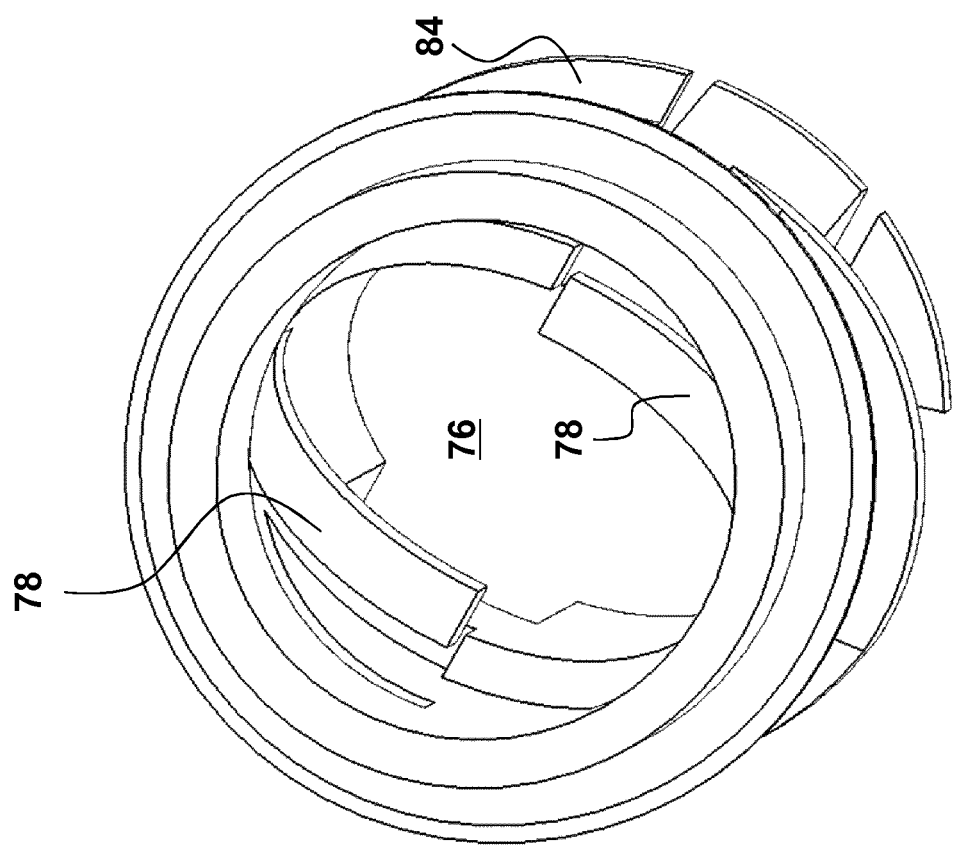
Fig. 9

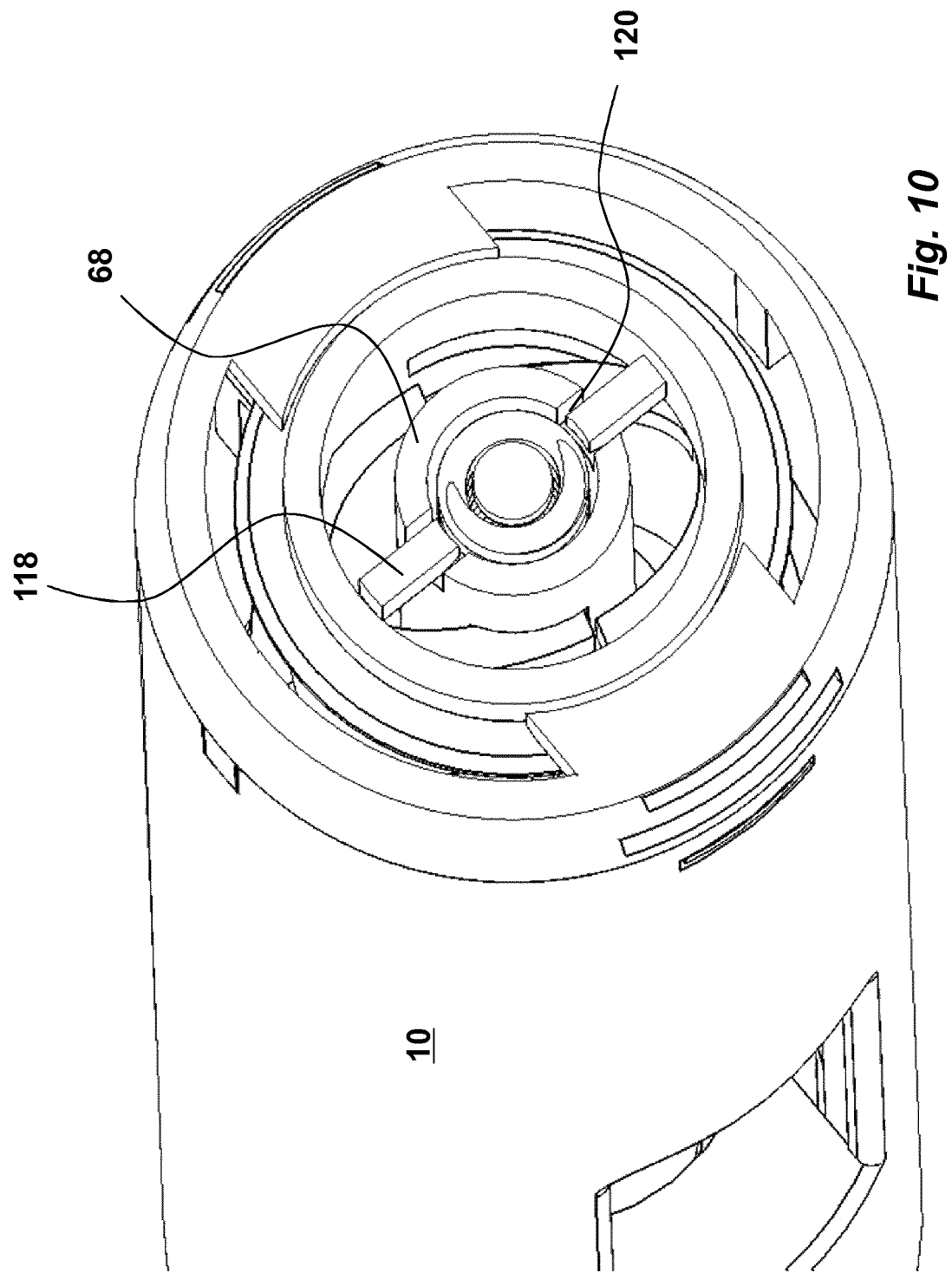

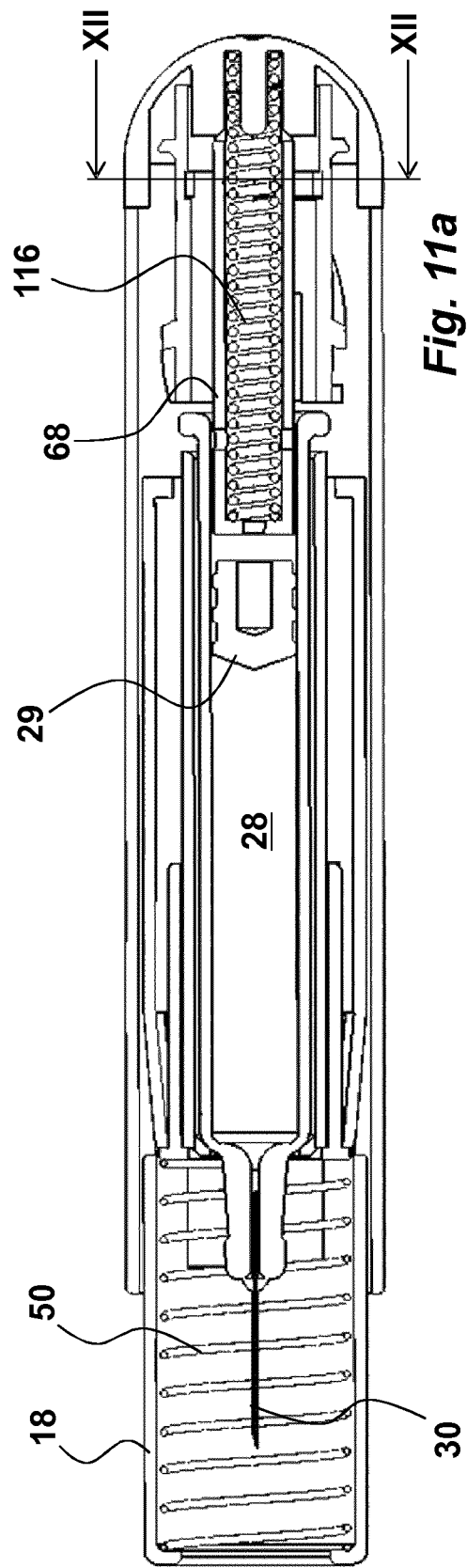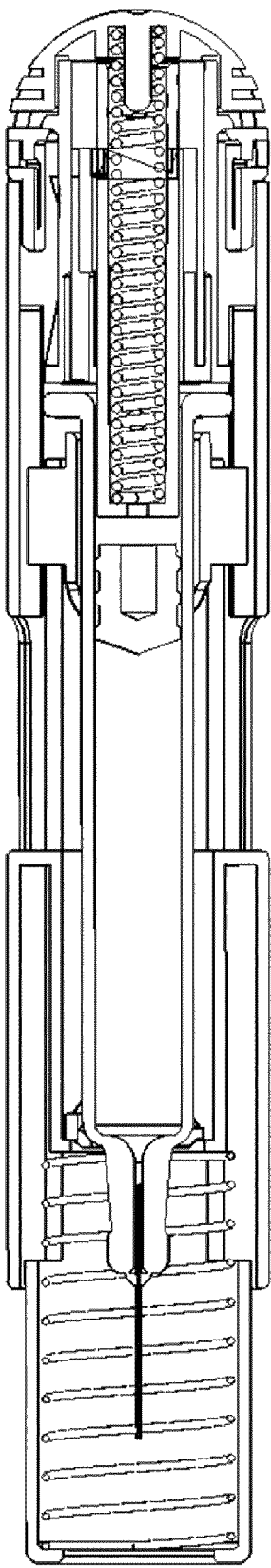
Fig. 11a
Fig. 11b

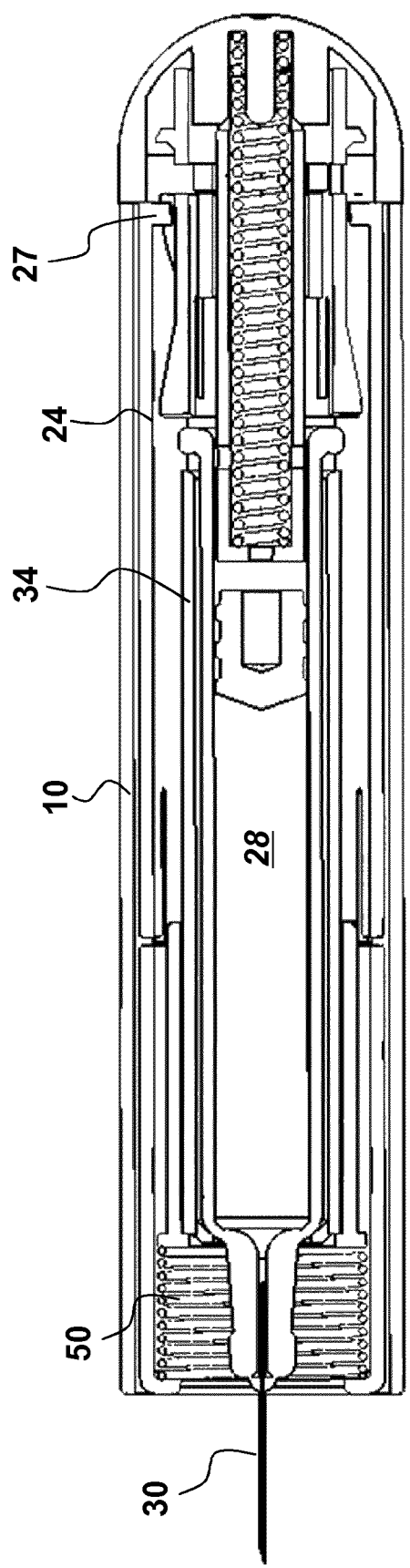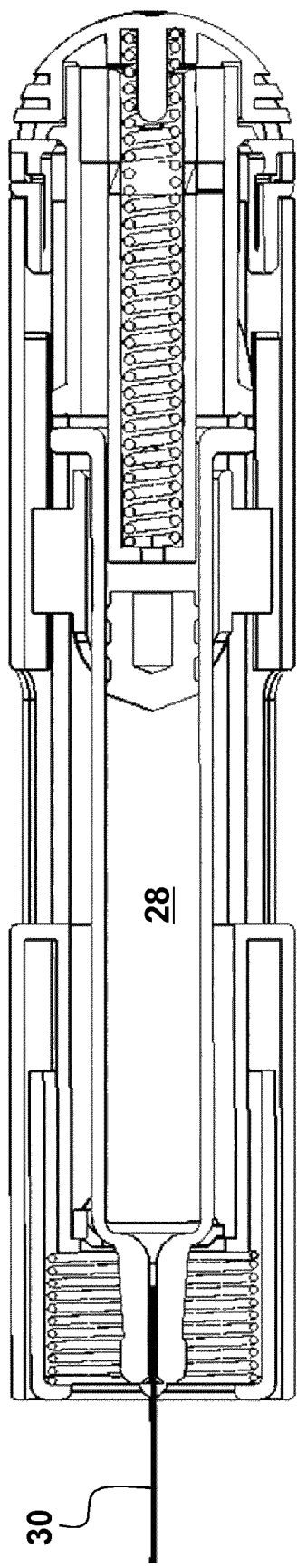

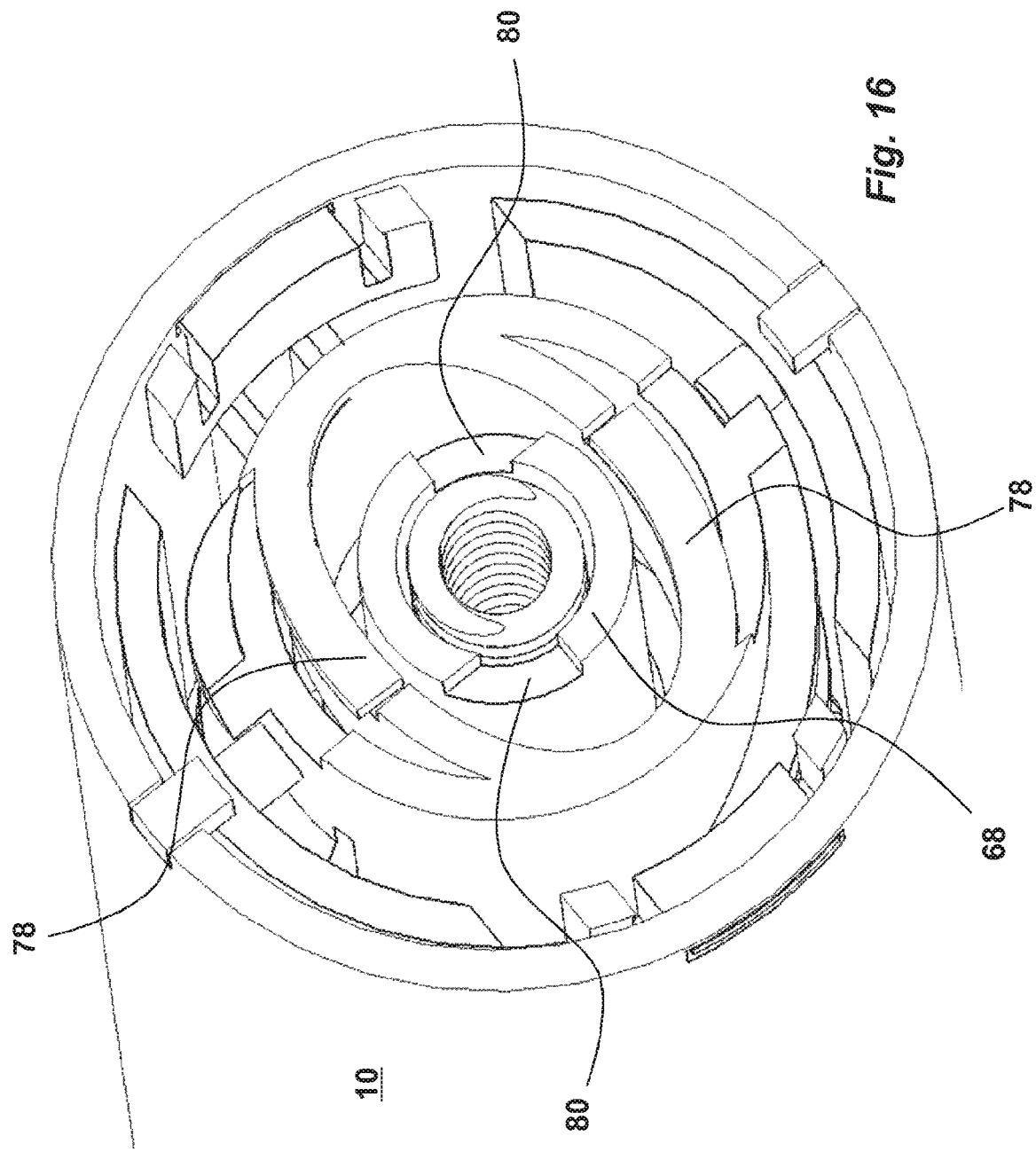

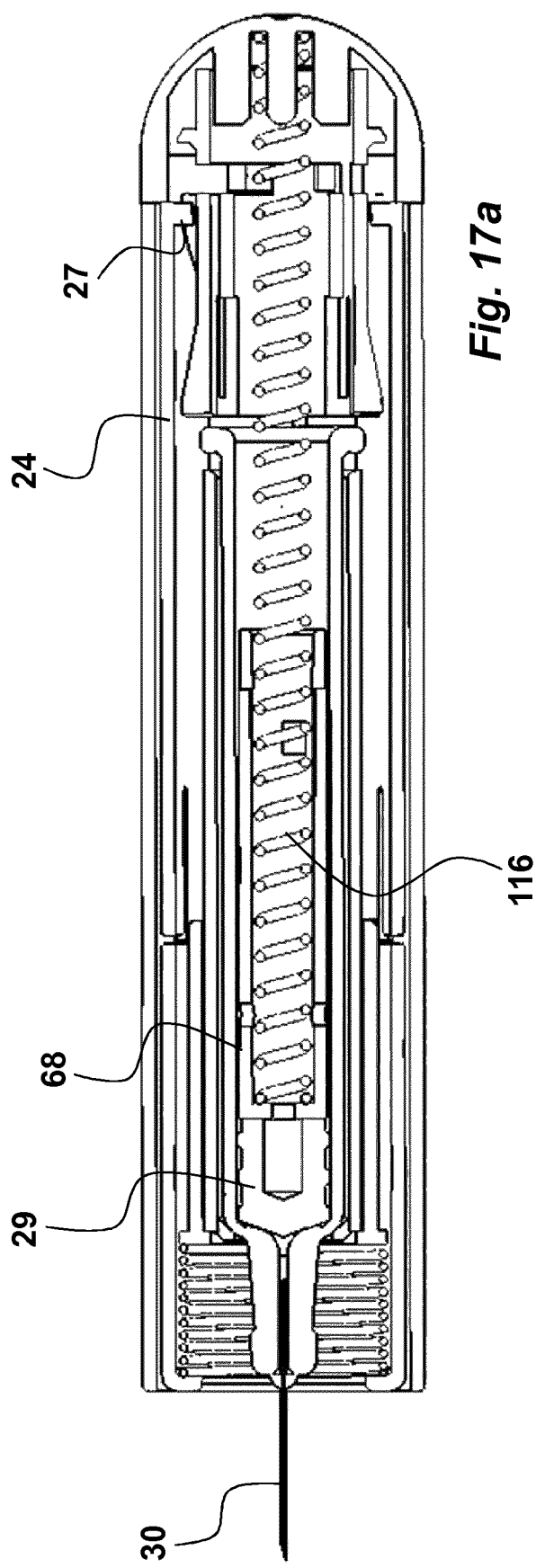
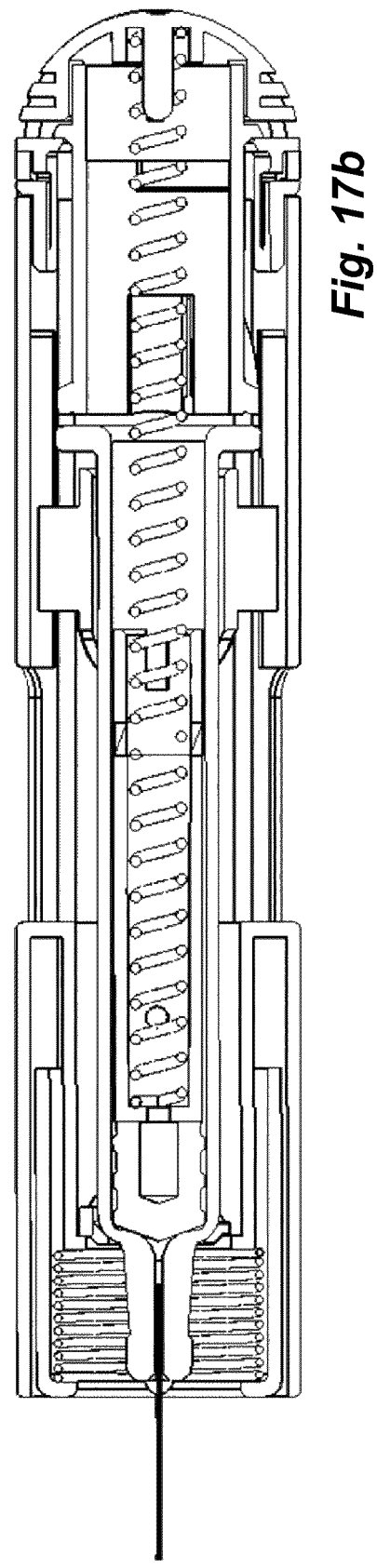
*Fig. 17a*
*Fig. 17b*

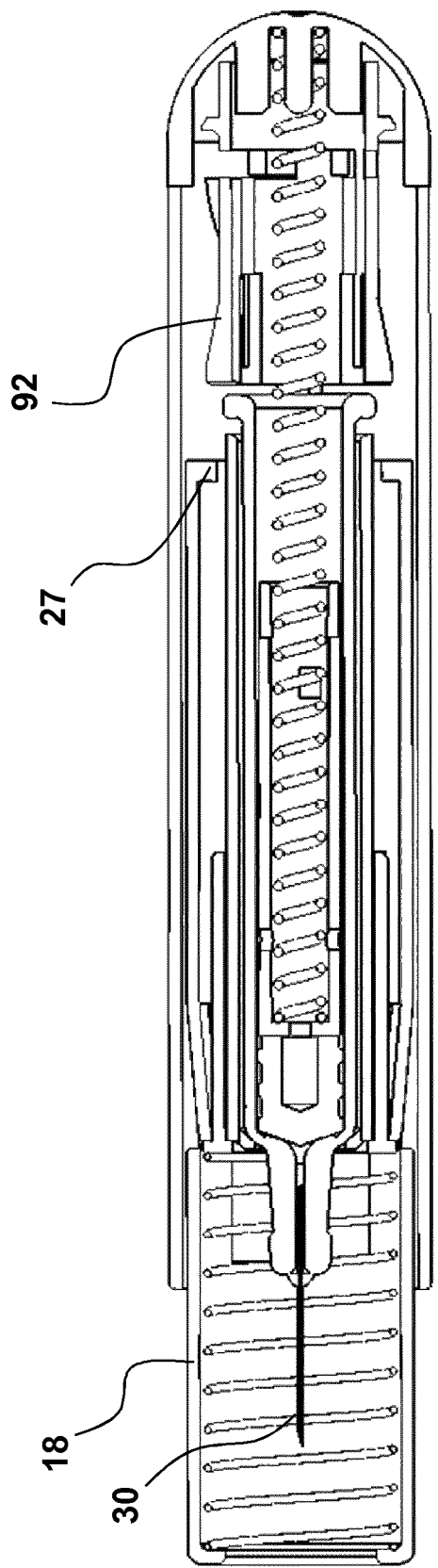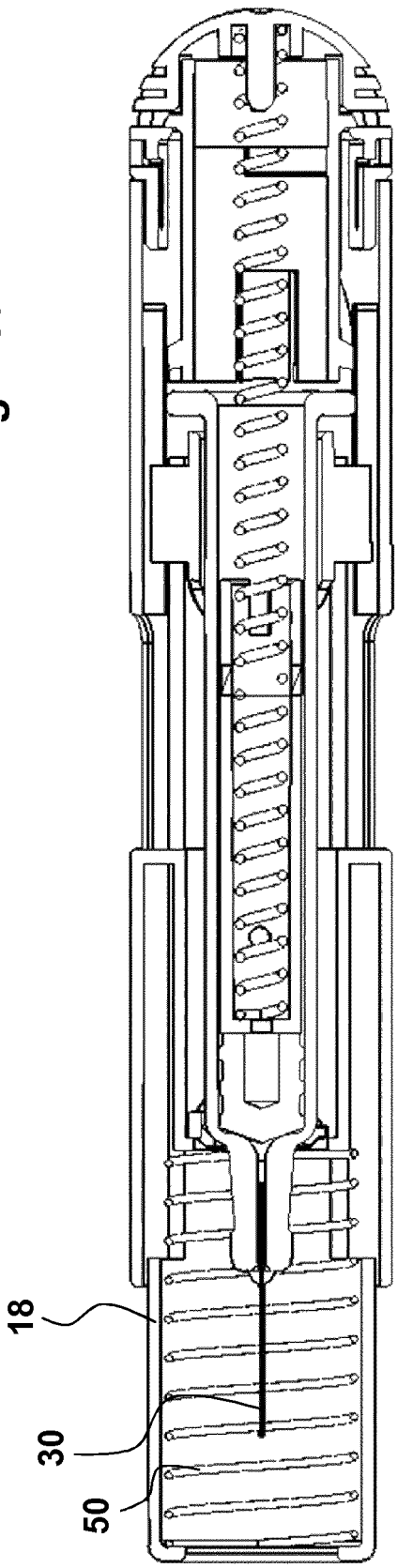
*Fig. 18a*
*Fig. 18b*

MEDICAMENT DELIVERY DEVICE WITH ROTATOR RETAINING THE PLUNGER ROD

CROSS-REFERENCE TO RELATED APPLICATIONS

The present application is a U.S. National Phase Application pursuant to 35 U.S.C. § 371 of International Application No. PCT/EP2015/058779 filed Apr. 23, 2015, which claims priority to Swedish Patent Application No. 1450532-5 filed May 6, 2014. The entire disclosure contents of these applications are herewith incorporated by reference into the present application.

TECHNICAL AREA

The present invention relates to a medicament delivery device and in particular a device that is robust, reliable and intuitive to use.

BACKGROUND OF INVENTION

There are a large number of medicament delivery devices on the market that are designed to be handled by a user or patient him-herself and not by medical staff. In order for the user to be able to handle the device confidently and securely it has to be rather intuitive and straightforward regarding its function.

Further, when taking production aspects in consideration, it is an advantage to keep the number of components as low as possible. A large number of components add to the complexity as well as cost. In this respect it is an advantage if one component is capable of performing more than one function.

Document WO2006/057604 discloses a medicament delivery device provided with a number of functions that will facilitate for the user. The functions comprise priming, injection, and handling of the needle shield. Most of these functions are handled by a so called tubular element, which is a generally tubular element arranged with ledges and protrusions. These ledges and protrusions are arranged to co-act with components of other elements for performing different functions when the tubular element is caused to turn.

Although the device according to WO2006/057604 has proved to function well, it still contains quite a few components which make the device complex both regarding manufacture and regarding interaction between the components. There is thus room for improvements regarding robustness, storage security, reliable activation correlation of number of components and number of functions.

BRIEF DESCRIPTION OF INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art devices. This aim is obtained with a medicament delivery device according to the independent patent claim. Preferable features and embodiments of the invention form subject of the dependent patent claims.

According to a main aspect of the invention, it comprises a medicament delivery device which extends along a longitudinal axis and comprises a generally tubular elongated housing having a proximal and a distal end, which generally tubular elongated housing is arranged to accommodate a medicament container. The medicament container may be arranged with a medicament delivery member through which medicament may be expelled. The medicament delivery member may either be integrated with the medicament container or be arranged attachable to the medicament container by suitable attachment elements. In this respect, the attachment elements may comprise a number of different solutions such as threads, bayonet connections, luer-connections, just to mention a few. The medicament delivery member may be a number of different elements such as injection needles, inhalation nozzles, nebulisers, needleless delivery elements, etc.

The medicament delivery device may further comprise a drive unit may comprise a drive element and a plunger rod operably arranged to act on said medicament container. The drive element may comprise a number of different designs and types that are suitable of providing a force on the plunger rod for urging it to act on the medicament container. These may comprise compression springs, clock springs, gas springs, torsion springs, etc. Also the medicament delivery device further comprises a tubular element rotatable arranged in relation to said housing. The tubular element is operably arranged to said plunger rod.

According to a favourable solution, the plunger rod comprises at least one holding member and the tubular element comprises at least one arm extending generally transversal to the longitudinal axis of the device. The at least one arm is arranged to engage the at least one holding member on said plunger rod to releasable hold said drive unit in an energy accumulated state. The energy accumulated state is a state wherein the drive element is loaded with energy, e.g. a pre-tensioning or compressing a spring, and wherein the plunger rod together with the tubular member are holding the loaded drive element.

According to another aspect of the invention, the generally tubular elongated housing comprises a proximal and a distal housing part wherein the plunger rod is rotationally locked to the distal housing part when the drive unit is the energy accumulated state.

According to a feasible solution, the at least one holding member on said plunger rod is a recess or a through hole or a slot or two parallel ledges extending generally transversal to the longitudinal axis of the device and configured to receive and hold the at least one flexible arm.

According to one aspect of the invention, the at least one arm is a rigid arm and wherein preferably the at least one arm is an axially rigid arm but radially flexible. The meaning of rigid is that the arm is rigid and robust in the longitudinal direction.

According to another aspect of the invention, the least one arm is arranged on the inner circumferential surface or on a rim of the tubular element.

According to a further aspect of the invention, the tubular element is arranged coaxially outside said plunger rod providing a direct interface between the plunger rod and the tubular element.

With those aspects a robust and straightforward functionality is obtained with very few components.

The medicament delivery device further comprises an activator displaceable arranged in relation to said housing and operably arranged to said tubular element such that displacement of said activator causes said tubular element to be rotated such that the at least one arm disengages from the at least one holding member on said plunger rod whereby the drive unit is released from the energy accumulated state. Thus, the tubular element is acting directly on the plunger rod for holding and releasing the latter when the activator causes the tubular element to rotate.

The activator is preferably slidable arranged along the longitudinal axis of the device between the housing and the tubular element. However, it is feasible that the activator is a manual activated button protruding through or from the housing and that it is either transversally or longitudinally slidable in relation to the longitudinal axis of the device.

Further, the activator comprises a medicament delivery member guard which is tubular shaped and configured to protrude a certain distance from the proximal end of the housing. The function of the medicament delivery member guard is to protect the medicament delivery member and keep it out of sight from a user.

Moreover, the tubular element comprises at least one interaction member on its outer circumferential surface and the activator comprises at least one activator element. The at least one interaction member is arranged to cooperate with the at least one activator element arranged on said activator. Further, the at least one interaction member is arranged inclined in relation to the longitudinal axis of the device.

A feasible solution in that respect is that the at least one interaction member comprises an inclined ledge and wherein said at least one activator element comprises a protrusion, which protrusion acts on said inclined ledge to rotate said tubular element when said activator is linearly displaced in relation to said housing when the proximal end of the medicament delivery member guard is pressed against a dose delivery site. Thus a generally linear movement in the distal direction of the medicament delivery member guard will cause a rotational movement of the tubular element, thus releasing the accumulated energy in the drive element and thereby forcing the plunger rod to move axially towards the proximal end of the device.

The activator is arranged with a resilient force member designed to return said activator with said medicament delivery member guard when the device is removed from a dose delivery site, thereby again protecting the medicament delivery member.

In order to increase the safety against unintentional contact with the medicament delivery member, said tubular element comprises a locking member arranged to interact with said at least one activator element on said activator for locking said activator when returned. In this way the functionality of the tubular element is further increased.

According to a feasible solution, said locking member is a flexible tongue having a stop ledge. This solution provides a robust and reliable locking of the medicament delivery member guard.

According to an important aspect of the invention is that the medicament delivery device according to the preceding features and feasible solutions, said device is preferably an injection device and said medicament delivery member is preferably an injection needle.

According to another important aspect of the invention is that the medicament delivery device is a disposable device.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 2a and 2b are cross-sectional longitudinal views of the device of FIG. 1 where FIG. 2b is taken 90 degrees in relation to FIG. 2a, and where FIG. 2b indicates a view "X-X" of the device shown in FIG. 10, FIG. 9 is a detailed view of components comprised in the device of FIG. 1, FIG. 10 is a detailed view of a different functional state of the device of FIG. 1, FIGS. 11a and 11b are cross-sectional longitudinal views of the device of FIG. 1 where FIG. 11b is taken 90 degrees in relation to FIG. 11a, and where FIG. 11a indicates a view "XII-XII" of the device shown in FIG. 12, FIG. 14b is taken 90 degrees in relation to FIG. 14a, FIG. 15 is a detailed view of a different functional state of the device of FIG. 1, FIG. 16 is a detailed view of a different functional state of the device of FIG. 1, FIGS. 17a and 17b are cross-sectional longitudinal views of the device of FIG. 1 where FIG. 17b is taken 90 degrees in relation to FIG. 17a, FIGS. 18a and 18b are cross-sectional longitudinal views of the device of FIG. 1 where FIG. 18b is taken 90 degrees in relation to FIG. 18a, FIG. 19 is a detailed view of a different functional state of the device of FIG. 1.

DETAILED DESCRIPTION OF THE INVENTION

Figure 1:
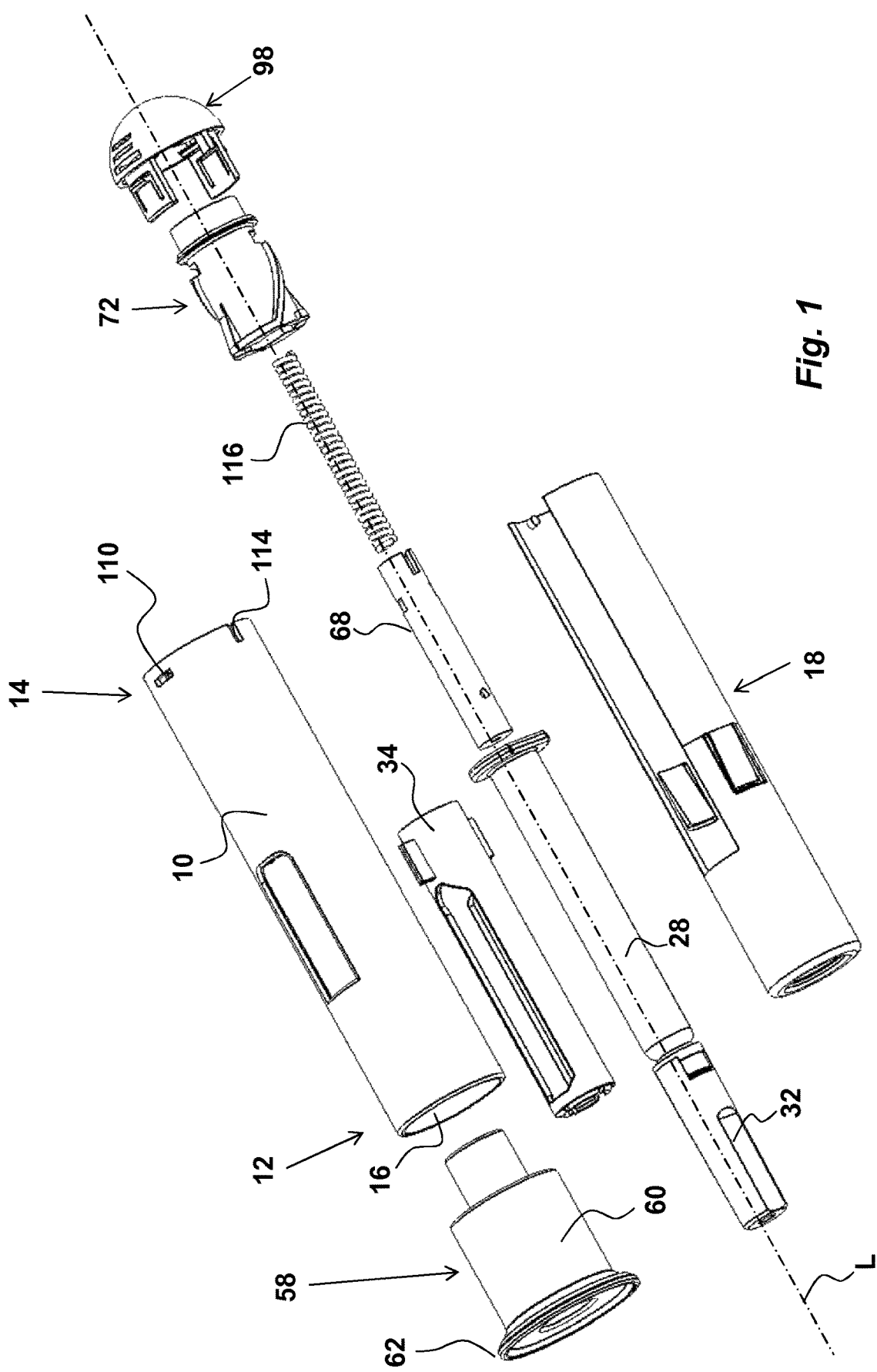
FIG. 1 is an exploded view of a medicament delivery device according to the invention.

A medicament delivery device which extends along a longitudinal axis L is shown in the drawings and comprises a generally tubular elongated housing having a proximal end and a distal end. In this respect it is to be understood that the housing may have a number of tubular shapes and a number of housing parts within the scope of the invention. As shown in the figures, the generally tubular elongated housing comprises a proximal housing part 10 having a proximal end 12 and a distal end 14, and a distal housing part 98 connected to the distal end 14 of the proximal housing part. It is to be understood that those two housing parts may also be one part. At the proximal end of the proximal housing part, a passage 16 is arranged. Through the passage 16, an activator 18 FIGS. 1 and 3, may be arranged slidable from an extended position to a retracted position relative the proximal housing part 10. The activator 18 comprises a medicament delivery member guard 20 at its proximal part having a generally tubular shape with a diameter somewhat smaller than the inner diameter of the proximal passage 16 of the proximal housing part 10. When the activator is in the extended position, at least a predetermined part of the medicament delivery member guard 20 is proximally protruding from the proximal end of the proximal housing and covering the medicament delivery member. When the activator is in the retracted position, at least a predetermined part of the medicament delivery member guard 20 is proximally protruding from the proximal end of the housing or is flush with the proximal end of the proximal housing part such that the medicament delivery member is uncovered.

Figure 3:
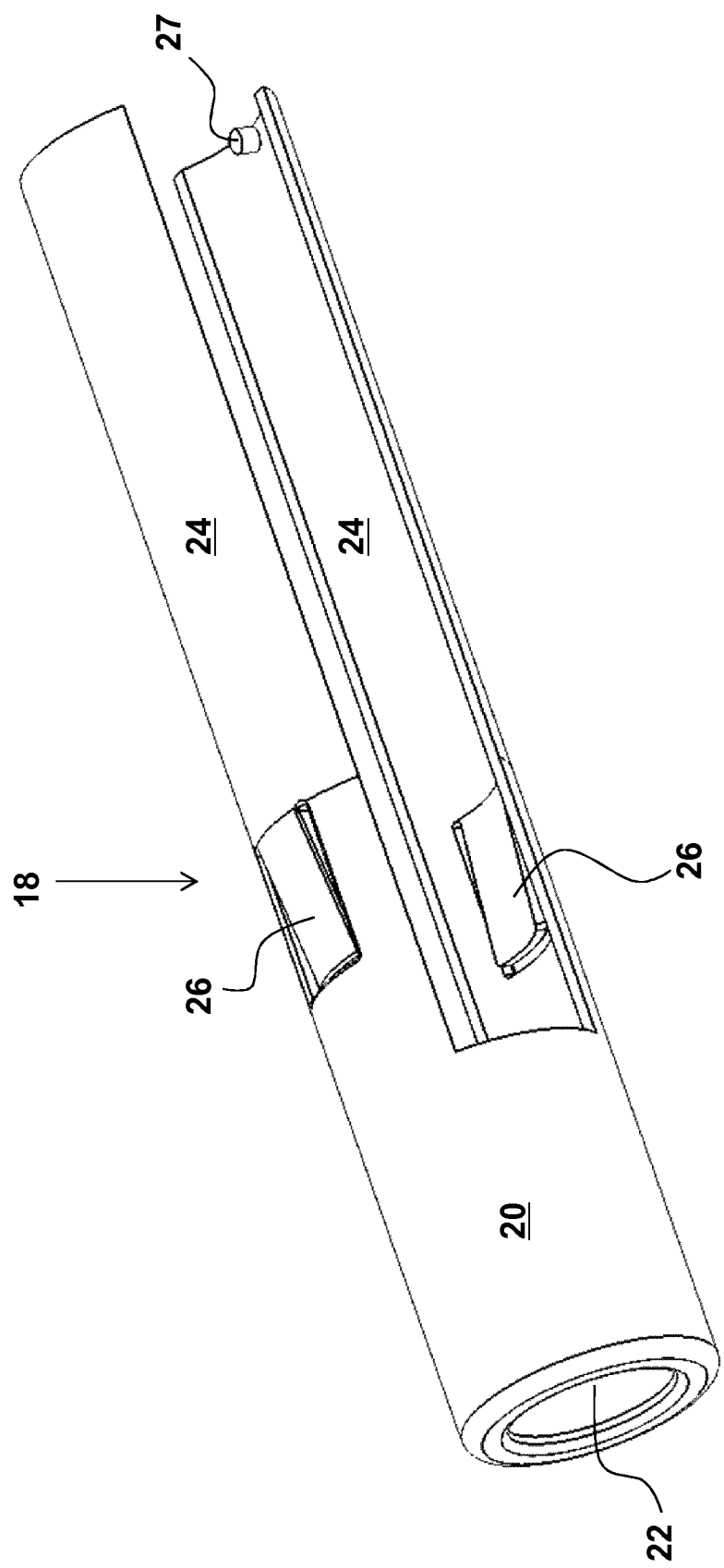
FIG. 3 is a detailed view of components comprised in the device of FIG. 1.

The activator 18 further comprises a central passage 22 and two distally directed arms 24 where the arms 24 have a curvature, as seen transversal to the longitudinal axis L, generally corresponding to the inner diameter of the proximal housing part 10. The arms 24 of the activator 18 are each arranged with a stop member 26 which in the present embodiments is a generally proximally directed tongue that is somewhat inclined inwards as seen in FIG. 3. The function of these stop members 26 will be explained below. The arms 24 are further arranged with activator elements 27 which in the present embodiment are radial inwardly extending protrusions on an inner, distal area as seen in FIG. 3. The function of these activator elements 27 will be explained below. It is however to be understood that the corresponding stop members 26 and the radial inwardly extending activator elements 27 may be of other types.

However, in a further embodiment (not shown) the activator is a manual activated button protruding through or from the housing and wherein said activator is either transversally or longitudinally slidable in relation to the longitudinal axis of the device.

The proximal housing part 10 is further arranged to accommodate a generally elongated tubular medicament container 28, FIG. 2, which medicament container 28 is provided with a stopper 29 movable in the longitudinal direction. In a further embodiment (not shown), the proximal housing part 10 is arranged to be connectable by suitable members to a medicament container housing. The medicament container is further arranged with a medicament delivery member 30, FIG. 2. In the embodiment shown the medicament delivery member 30 is an injection needle integrated with the medicament container 28. It is however to be understood that the medicament delivery member 30 may be of other types. It is further to be understood that the medicament delivery member 30 may be arranged attachable to the medicament container by different types of attachment elements such as threads, bayonet connections, luer-connections etc.

The medicament delivery member 30 is further protected by a medicament delivery member shield 32, FIGS. 1 and 2. In the embodiment shown, the medicament delivery member shield 32 is in the form of a so called rigid needle shield or RNS. It is however to be understood that other types of medicament delivery member shields 32 may be used, such as so called soft needle shields, or SNS or flexible needle shields or FNS, or other suitable types capable of protecting the medicament delivery member before use, and in particular keeping the medicament delivery member 30 sterile.

Figure 4:
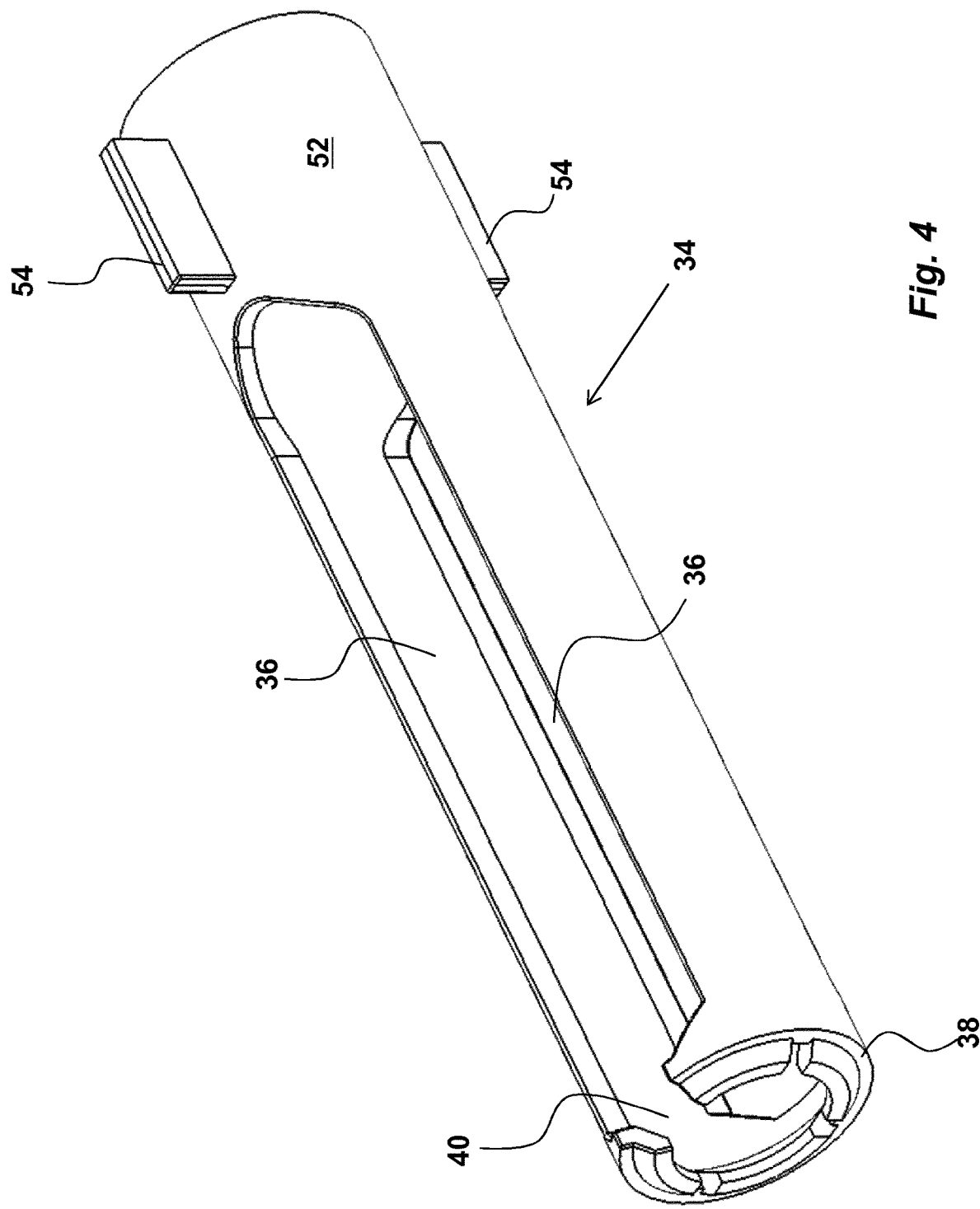
FIG. 4 is a detailed view of components comprised in the device of FIG. 1.

The medicament container 28 is intended to be held in position inside the proximal housing part preferably by a medicament container holder 34, FIGS. 1 and 4. The medicament container holder 34 is arranged as a generally tubular body arranged with elongated windows 36 on opposite sides of the body. The proximal end of the medicament container holder 34 is arranged with an inwardly extending circumferential ledge 38, FIG. 4. The ledge is arranged with a cut-out 40 to one of the windows 36 in order to enable insertion of a medicament container 28 inside the medicament container holder 34, where the circumferential ledge 38 is intended to act as a stop surface against a proximally directed neck surface of the medicament container 28.

Figure 5:
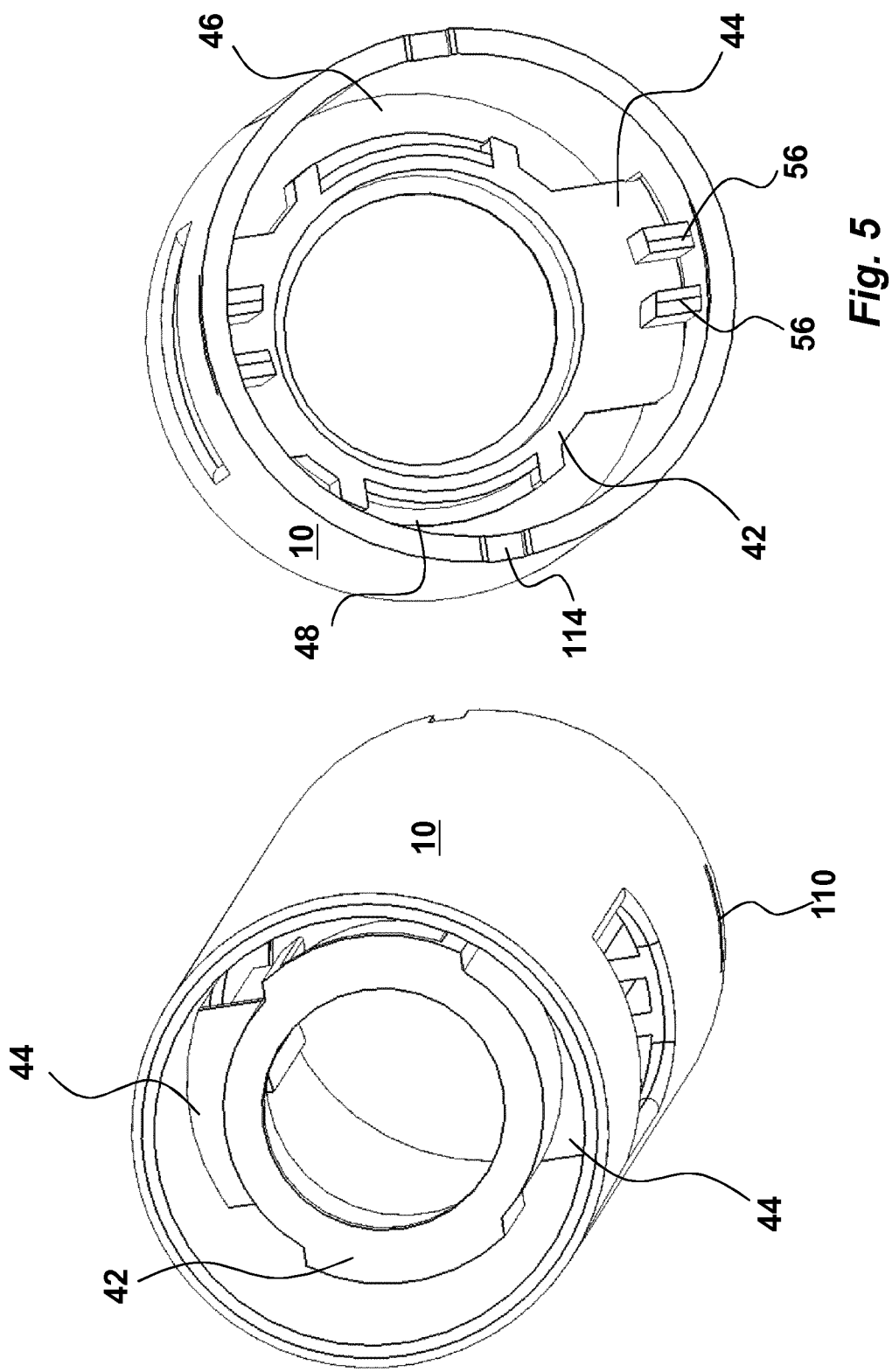
FIG. 5 is a detailed view of components comprised in the device of FIG. 1.

The proximal surface of the circumferential ledge 38 is further intended to be in contact with a distally directed surface of a generally ring-shaped stop element 42, FIG. 5, inside the proximal housing part 10 at the proximal area thereof. The stop element 42 is attached to the inner surface of the proximal housing part 10 by two oppositely arranged bridges 44, thereby creating passages 46 on either side of the bridges 44 for the arms 24 of the activator 18. The stop element 42 is further arranged with recesses 48 on its distally directed surface along its outer edge, one recess adjacent each passage, wherein the recesses 48 are intended to accommodate the proximal, free ends of the stop members 26, e.g. the tongues, of the activator 18, whereby the activator 18 is prevented from being moved in the proximal direction by a resilient force member 50 that is arranged between a distally directed ledge arranged around the passage 22 of the activator 18 and proximally directed surfaces of the bridges 44, FIG. 2. It is however to be understood that the resilient force member 50 may a spring of different types.

The medicament container holder 34 is further arranged with a distal, generally tubular part 52. On the outer surface of the tubular part 52, generally radially outwards extending support elements 54 are arranged, positioned on opposite sides. The support elements 54 have such a height that they come in contact with the inner surface of the proximal housing part 10. Further the inner surface of the proximal housing part 10 is arranged with two pairs of parallel ledges 56, FIG. 5, extending in the longitudinal direction, between which the support elements 54 fit, wherein the distance between the ledges 56 are somewhat larger than the thickness of the support elements 54, whereby a rotational lock of the medicament container holder 34 is obtained in relation to the proximal housing part 10.

It is however to be understood that the proximal housing part may have integral supports for receiving the medicament container 28 and there is no need to have a medicament container holder.

Figure 6:
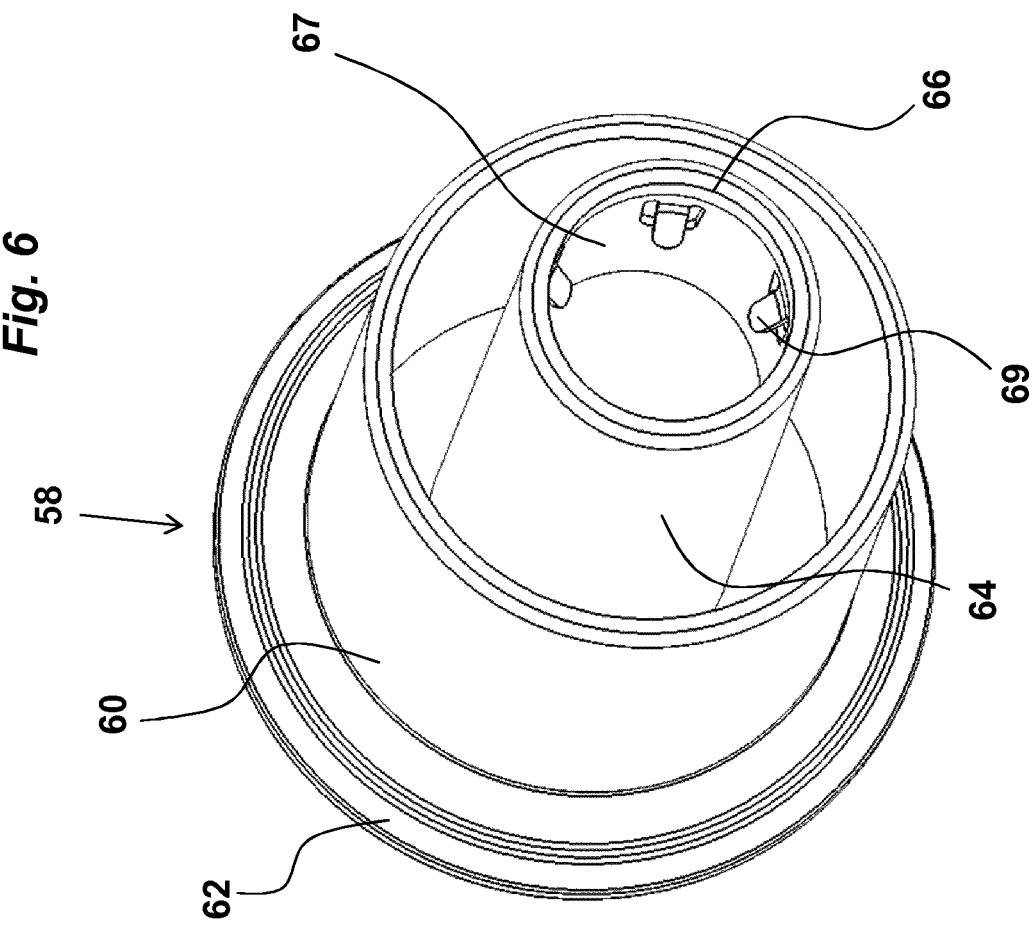
FIG. 6 is a detailed view of components comprised in the device of FIG. 1.

A safety cap 58, FIGS. 1 and 6, is further arranged to be releasibly attached to the proximal end of the activator 18. It is however to be understood that the safety cap 58 may also be releasably attached to the proximal end of the proximal housing part or to a both the proximal end of the activator and the proximal housing part. The safety cap 58 comprises a generally tubular body 60 provided with an outwardly extending ledge 62 intended to facilitate gripping of the safety cap. The safety cap 58 is further arranged with a central element 64, which has a generally tubular shape extending in the distal direction and having a diameter somewhat larger than the outer diameter of the medicament delivery member shield 32. The distal end of the central element 64 is arranged with an inwardly extending ledge 66.

Further a removal element 67 is provided in the safety cap 58. The removal element 67 comprises a generally tubular body having an outer diameter generally corresponding to the inner diameter of the central element 64, wherein the removal element 67 is placed such inside the central element 64 that a distally directed edge of the removal element 67 is in contact with the inwardly ledge 66 of the central element 64. The removal element 67 is further arranged with inwardly inclined, generally proximally directed, tongues 69, which tongues 69 are intended to come in contact with the outer surface of the medicament delivery shield 32, as will be described.

A drive unit is also arranged in the device. The drive unit comprises a drive element 116 and a plunger rod 68 operably arranged to act on said medicament container. The drive element 116 may comprise a number of different designs and types that are suitable for accumulating energy and providing a force on the plunger rod for urging it to act on the medicament container. As shown in the figures, the drive element 116 is a compression spring. It is to be understood that the drive element may comprise, clock springs, gas springs, torsion springs, etc. Also the medicament delivery device further comprises a tubular element 72 which is rotatable arranged in relation to said generally tubular elongated housing as it will be explained below.

Figure 7:
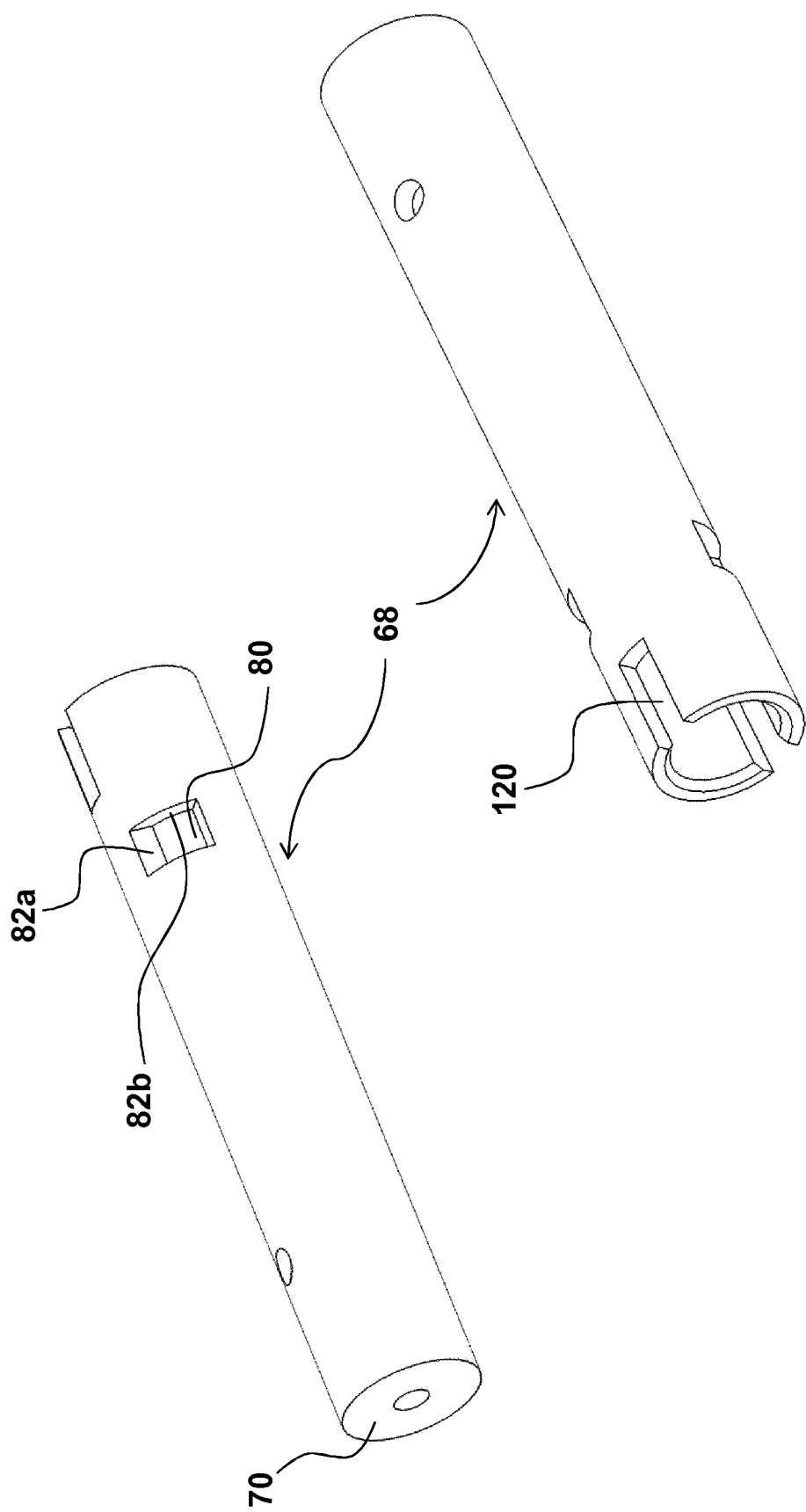
FIG. 7 is a detailed view of components comprised in the device of FIG. 1.

The plunger rod 68, FIGS. 1 and 7, is in the form of an elongated tubular element having a proximal end wall 70 intended to be in contact with the stopper 29 of the medicament container 28. The plunger rod comprises at least one holding member 80, wherein the at least one holding member 80 on said plunger rod 68 is a recess. However it is understood that in further embodiments, the at least one holding member 80 may be a through hole or a slot or two parallel ledges extending generally transversal to the longitudinal axis of the device.

Figure 8:
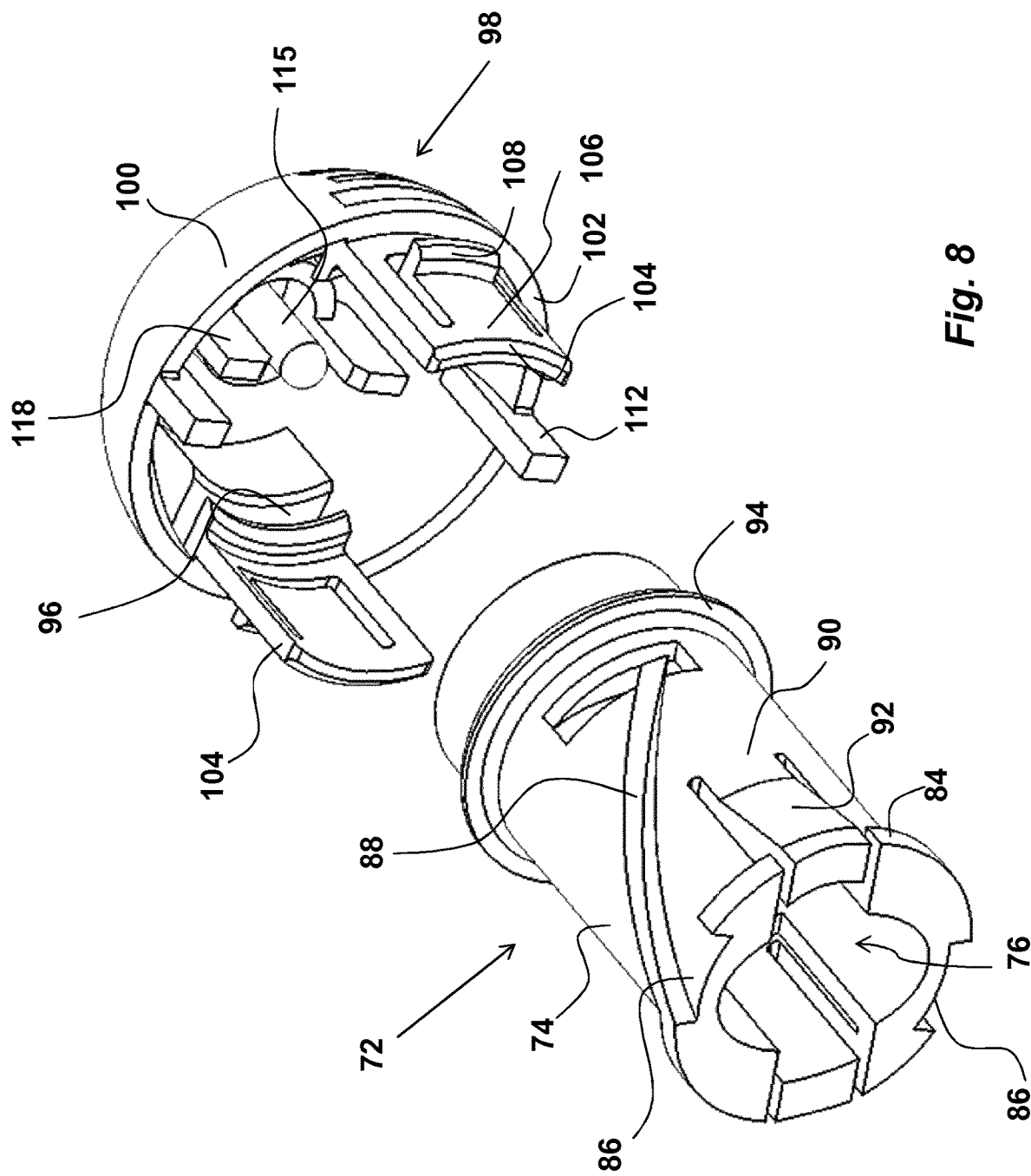
FIG. 8 is a detailed view of components comprised in the device of FIG. 1.

The tubular element 72, shown in the present embodiment, is designed as a generally tubular body 74 with a central passage 76 through which the plunger rod extends, FIGS. 1, 8 and 9. The passage 76 may have a generally oval shape as seen in FIG. 9, where the shortest cross-measure d is somewhat larger than the diameter of the plunger rod 68, but it is understood that it may be possible to have other type of shapes. The tubular element 72 comprises at least one arm extending generally transversal to the longitudinal axis of the device. As seen in FIG. 9, the inner surface of the tubular element 72 is arranged with arms 78 extending generally transversal to the longitudinal axis of the device. The arms 78 are arranged generally in the circumferential direction of the passage 76 and are positioned opposite each other. In an initial position, the arms 78 are positioned somewhat inwards inclined as seen in FIG. 9. In another embodiment, FIG. 21, the arms 78 are arranged on a rim of the tubular element 72 and extend extending generally transversal to the longitudinal axis L of the device.

As shown in the FIG. 7, the arms 78 are intended to fit into holding members 80 which are generally rectangular recesses on the outer surface of the plunger rod 68, where one side wall 82a of the rectangular recess is somewhat inclined with respect to a radial direction in order to facilitate the positioning of the arms 78 inside the recesses 80. Further a proximally directed side wall 82b of the recess 80 acts as a stop ledge when the arms 78 are positioned in the recesses 80 as will be described.

Further, the proximal end of the tubular element 72 is arranged with a circumferential support ledge 84 intended to support the tubular element 72 in relation to the proximal housing part 10. The circumferential support ledge 84 is provided with two cut-outs 86, placed on opposite sides, in order to house the activator elements 27, e.g. the protrusions, of the arms 24 of the activator 18 as will be described. Adjacent one of the edges of the cut-outs 86, an interaction member 88, FIG. 8, is extending in the distal direction having an inclination in relation to the longitudinal axis L of the device. A shown in FIG. 8 the interaction member 88 is an inclined ledge, but it is to be understood that the interaction member may have another type of shape. Further, locking members 90 in the form of two flexible tongues or arms are arranged at a distance in the circumferential direction of the cut-outs 86, where the flexible tongues or arms are positioned on opposite sides of the tubular element 72. The locking members 90 extend in the proximal direction and are arranged flexible in a generally radial direction. The free ends of the locking members 90 are provided with stop ledges 92 in the form of wedge-shaped protrusions, with the inclined surfaces of the wedge-shaped protrusions in the distal direction. At the distal area of the tubular element 72, a circumferential ridge 94 is arranged. The ridge 94 is intended to fit into grooves 96 arranged on an inner surface of the distal housing part 98 of the device, FIG. 8.

The distal housing part 98 has a main body 100 that in the embodiment shown is designed as a dome. The body 100 of the distal housing part 98 has a proximally directed end surface 102, FIG. 8, that is intended to be in contact with a distally directed end surface of the proximal housing part 10 when the distal housing part 98 is connected to the proximal housing part 10. The body 100 is further arranged with proximally directed plate-like projections 104 that are intended to extend into the distal end of the proximal housing part 10. The projections 104 are in turn arranged with distally directed tongues 106 that are arranged flexible in the generally radial direction of the proximal housing part 10. The free ends of the tongues 106 are arranged with outwardly arranged protrusions 108, which protrusions 108 are intended to fit into cut-outs 110 in the distal area of the proximal housing part 10, for locking the distal housing part 98 to the proximal housing part 10. The proximally directed end surface 102 of the body of the distal housing part 98 is further arranged with proximally directed, generally rectangular, protrusions 112, which protrusions are intended to fit into correspondingly shaped cut-outs 114 in the distal end surface of the proximal housing part 10, for providing a rotational lock of the distal housing part 98 in relation to the proximal housing part 10.

The inner surface of the body 100 of the distal housing part 98 is further arranged with a central, proximally directed protrusion 115. It is intended to extend proximally into a distal part of the drive element 116, FIG. 2, that is to be compressed between the inner surface of the body 100 of the distal housing part 98 and a distally directed surface of the end wall 70 of the plunger rod 68. Further, in the shown embodiment two generally rectangular protrusions 118 are arranged on each side of the central protrusion 115, which rectangular protrusions 118 extend in the proximal direction. These rectangular protrusions 118 are intended to cooperated with two cut-outs 120 having corresponding shapes, arranged on a distally directed end surface of the plunger rod 68, FIG. 7, for providing a rotational lock between the plunger rod 68 and the distal housing part 98, as seen in FIG. 10 and as will be described.

Figure 20:
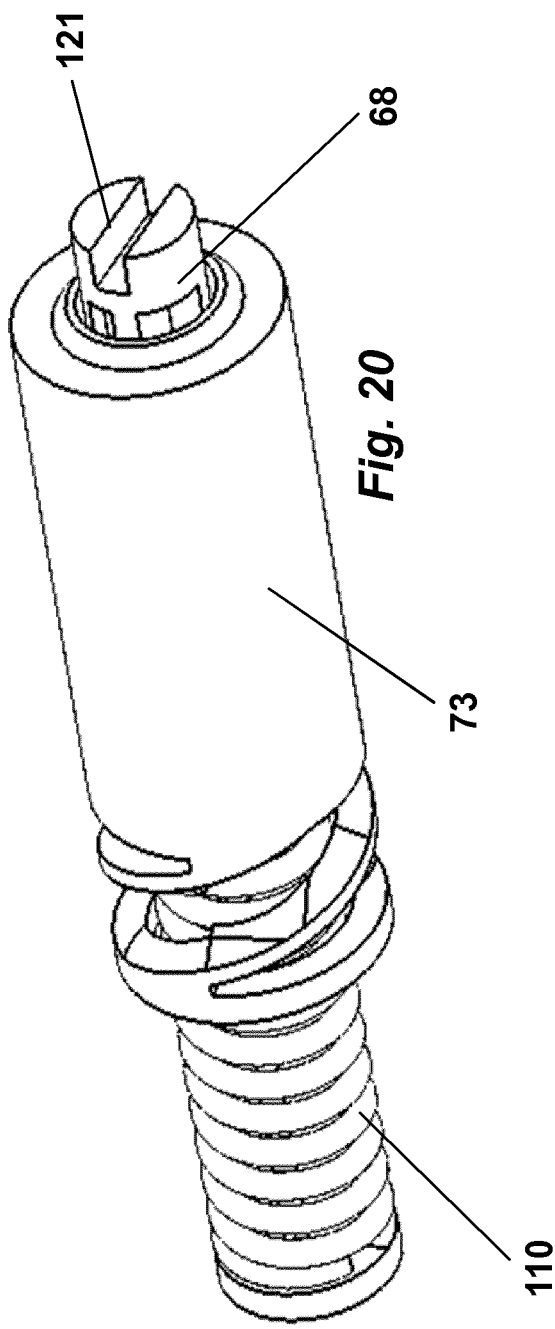
FIG. 20 is a detailed view of a different functional state of the device of FIG. 1.
Figure 21:
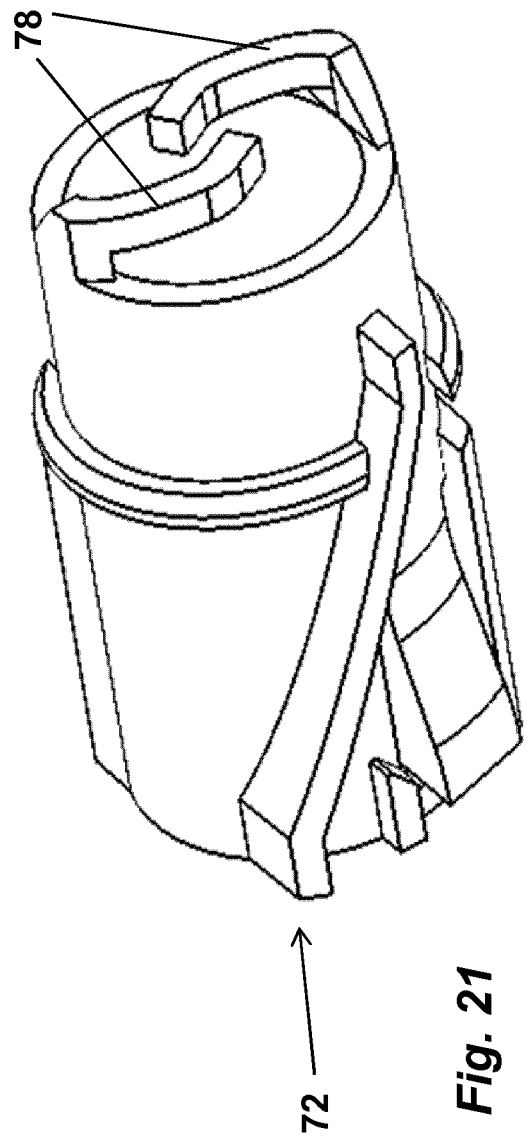
FIG. 21 is a detailed view of a different functional state of the device of FIG. 1.

In a further embodiment, the drive element 116 may be partially surrounding the outer surface of the plunger rod 68, FIG. 20. A further tubular component 73, FIG. 21, is placed and supported coaxially inside the tubular element 72 such that the drive element 116 is compressed between a circumferential ledge of the further tubular component and a distally directed ledge arranged around the outer surface on the proximal end of the plunger rod. Further, one generally rectangular protrusion may be arranged on the inner surface of the distal housing part 98 and said protrusion extends in the proximal direction. This rectangular protrusion is intended to cooperate with a slot 121, FIG. 20, having corresponding shape, arranged on a distally directed end surface of the plunger rod 68, for providing a rotational lock between the plunger rod 68 and the distal housing part 98.

Thus, the drive unit is in an energy accumulated state when the tubular element 72 is held by the generally elongated housing, more particularly by the proximal housing part 10; when the plunger rod is rotationally locked to the generally elongated housing, more particularly to the distal housing part 98; when the drive element 116 is loaded with energy; and when the arms 78 of the tubular member are engaged to the holding members on said plunger rod as described above.

Figure 12:
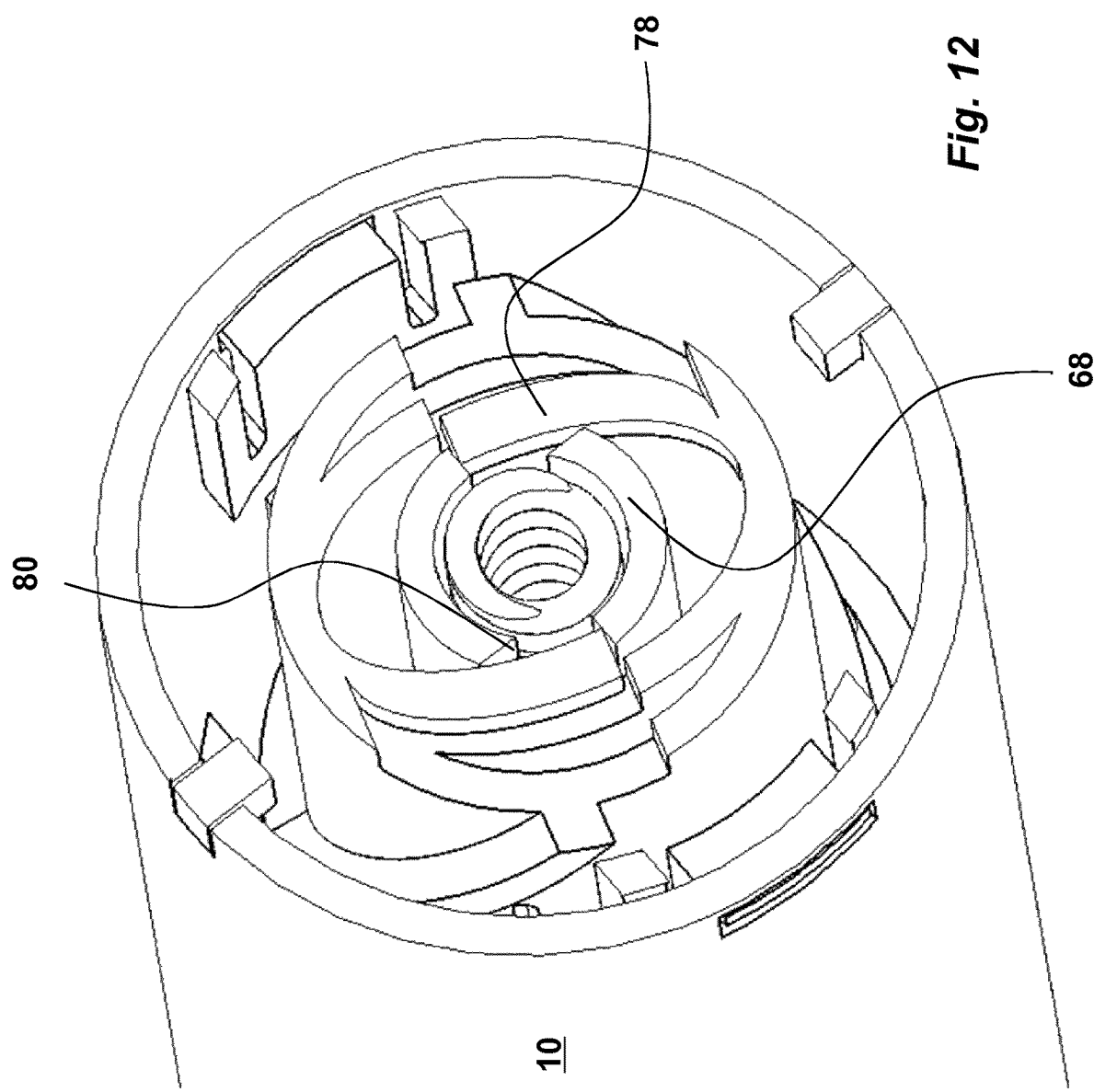
FIG. 12 is a detailed view of a different functional state of the device of FIG. 1.

The device is intended to function as follows. When the device is delivered to a user, the activator 18 is in the extended position. The safety cap 58 is connected to the proximal end of the device with its central element 64 extending into the medicament delivery member guard 20 and surrounding the RNS 32, wherein the inclined tongues 69 of the removal element 67 is positioned in engagement with the outer surface of the RNS, FIG. 2. The drive unit is in the energy accumulated state as seen in FIG. 2. Thus, the plunger rod 68 is held by the arms 78 of the tubular element 72 being positioned in the holding members 80, e.g. rectangular recesses, of the plunger rod 68, FIG. 12. The plunger rod 68 is further rotationally locked by the rectangular protrusions 118 of the distal housing part 98 that are in engagement with the cut-outs 120 in the distal end of the plunger rod 68, FIG. 10.

Figure 13:
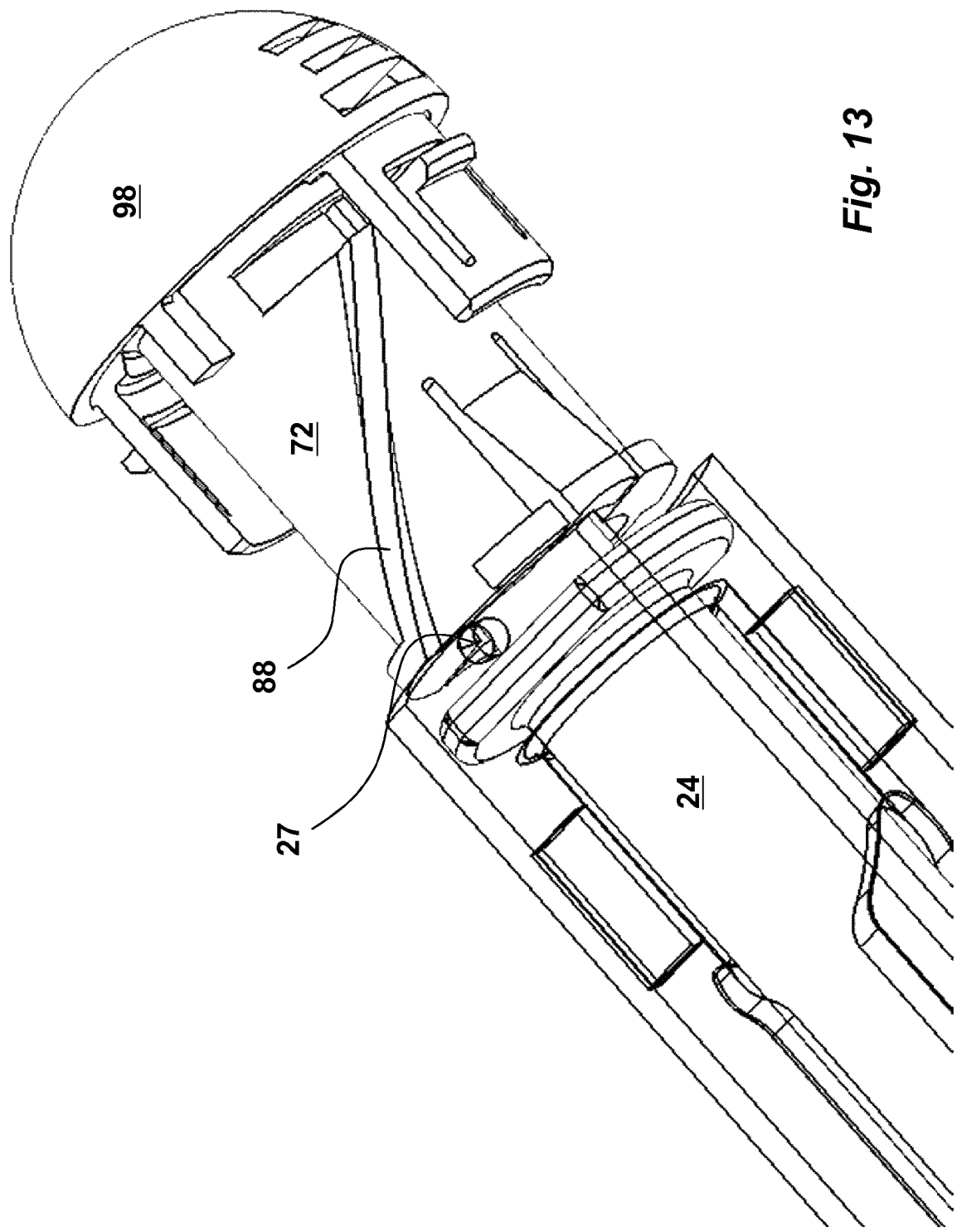
FIG. 13 is a detailed view of a different functional state of the device of FIG. 1, FIGS. 14a and 14b are cross-sectional longitudinal views of the device of FIG. 1 where

When the device is to be used, the user grips the safety cap 58 and pulls it in the proximal direction from the device, whereby the safety cap 58 is removed. Due to the connection with the medicament delivery member shield 32 via the tongues 69 of the removal element 67, the medicament delivery member shield is also removed, as seen in FIG. 11. As seen, the medicament delivery member guard 20 is in the extended position due to the resilient force member 50 and the activator elements 27, e.g. the protrusions on the arms 24 are positioned in relation to the tubular element 72 as seen in FIG. 13.

The next step is to position the device at the dose delivery site and press it towards the site. This will cause the proximal housing part 10 to be moved proximally in relation to the activator 18 and thus the medicament container holder 34 and the medicament container 28 with its medicament delivery member 30, thereby causing a penetration of the skin of the patient when an injection needle is used, as is shown in FIG. 14. The resilient force member 50 is compressed by the relative movement between the proximal housing part 10 and the activator 18, FIG. 14.

Figure 15:
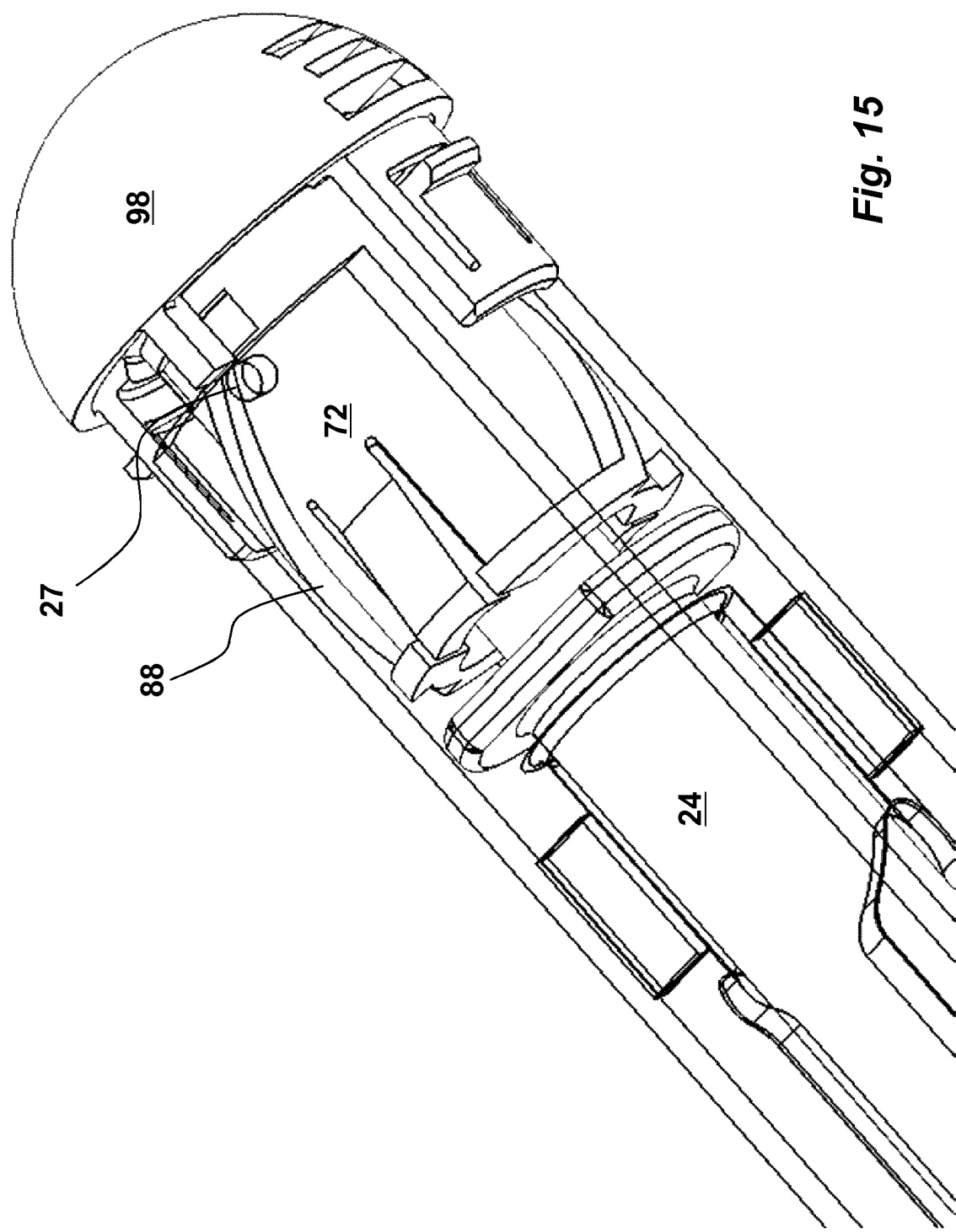

During the movement of the proximal housing part 10 in relation to the activator 18, the activator elements 27, e.g. the protrusions, of the arms 24 come in contact with the interaction members 88, e.g. the inclined ledges, of the tubular element 72, FIG. 15, and during the relative movement between activator elements 27 and the interaction members 88, the tubular element 72 will rotate in relation to the generally elongated housing. This will cause the arms 78 of the tubular element 72 to move out of engagement with the stop ledges 82*b* of the recesses 80 of the plunger rod 68, as seen in FIG. 16. Since, the plunger rod is rotationally locked to the generally elongated housing, more particularly to the distal housing part 98; the plunger rod will not rotate. Thus, the drive unit is released from the energy accumulated state i.e. the plunger rod 68 is released from the tubular element 72 and will be forced in the proximal direction by the accumulated energy in drive element 116, FIG. 17. The accumulated energy in the drive unit will move the stopper 29 inside the medicament container in the proximal direction, causing delivery or expelling of medicament through the medicament delivery member 30.

When the delivery sequence has ended, the device can be removed from the delivery site. This will cause the activator 18 to move in the proximal direction in relation to the generally tubular elongated housing due to the expansion of the resilient force member 50, FIG. 18. The movement of the activator 18 will cause the activator elements 27, e.g. the protrusions of the arms 24 to move in the proximal direction in relation to the tubular element 72, whereby the activator elements 27, e.g. the protrusions of the arms 24 will come in contact with and move over the stop ledges 92, more particularly over the wedge-shaped protrusions of the locking members 90 of the tubular element 72, whereby the locking members flex inwards radially.

Figure 19:
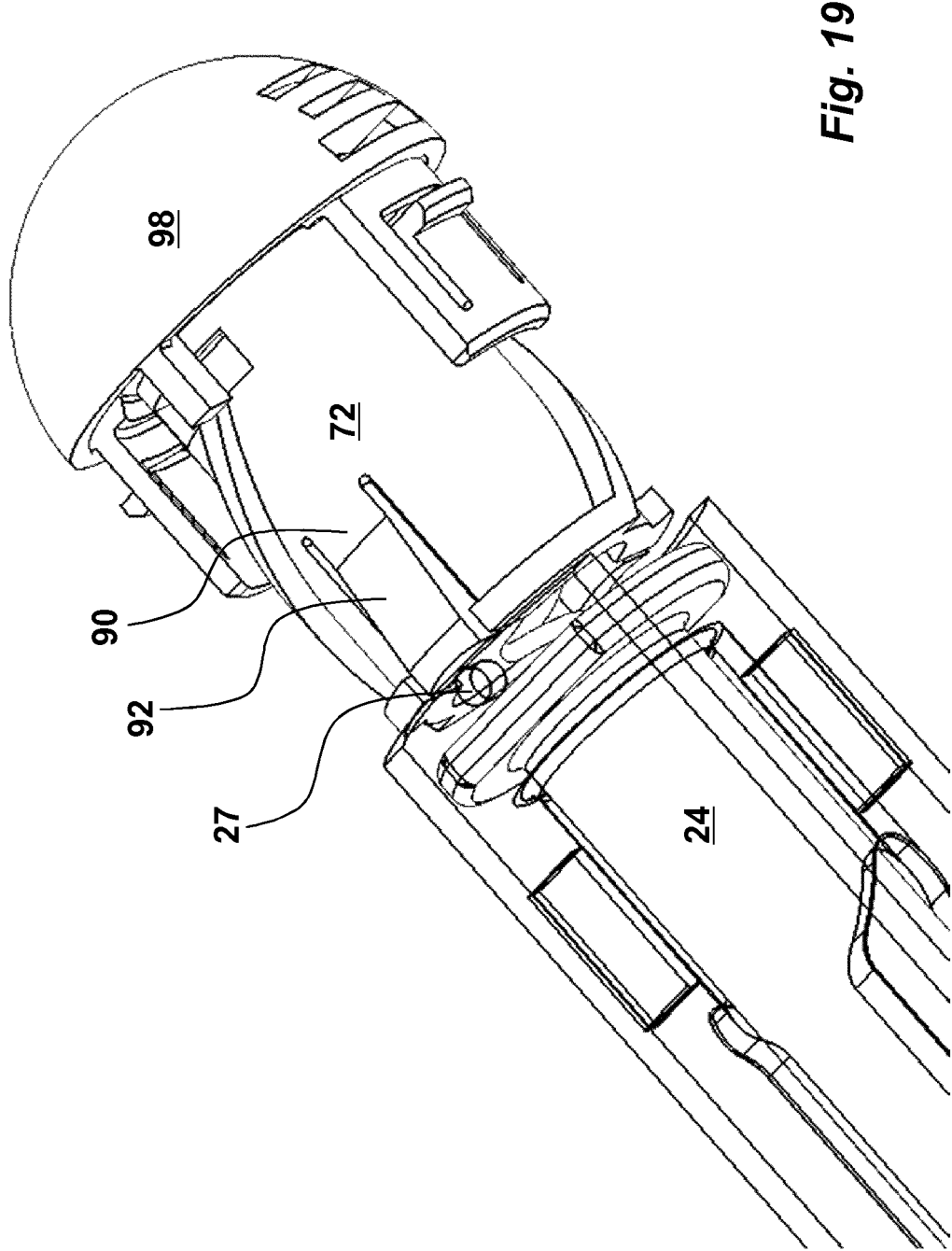

When the activator elements 27 of the arms 24 have passed the stop ledges 92, more particularly, the wedge-shaped protrusions, the locking members 90, more particularly, the flexible tongues or arms of the tubular element 72 will flex back outwards, whereby the proximally directed surface of the stop ledges 92 will prevent any movement in the distal direction of the activator 18 in relation to the generally elongated housing, thus locking it in the initial extended position, FIG. 19. The medicament delivery member 30 is thereby guarded by the proximal part of the activator 18. The device may now be discarded.

It is to be understood that the embodiment described above and shown in the drawings is to be regarded only as non-limiting examples of the invention and that it may be modified in many ways within the scope of the patent claims.

The invention claimed is:

1. A medicament delivery device which extends along a longitudinal axis and comprises:
    a generally tubular elongated housing having a proximal end and a distal end, wherein said generally tubular elongated housing is arranged to accommodate a medicament container;
    a drive unit comprising a drive element and a plunger rod operably arranged to act on said medicament container; and
    a tubular element rotatably arranged in relation to said generally tubular elongated housing and operably arranged to said plunger rod, wherein the plunger rod comprises at least one holding member and the tubular element comprises at least one arm extending generally transversal to the longitudinal axis of the medicament delivery device, wherein the at least one arm is arranged to engage the at least one holding member on said plunger rod to releasably hold said drive unit in an energy accumulated state, and wherein the at least one holding member of said plunger rod is at least one recess or at least one through hole or at least one slot comprising a side wall that is inclined in a radial direction to facilitate positioning the at least one arm in engagement with the at least one holding member, wherein said generally tubular elongated housing further comprises a proximally-directed protrusion at said distal end, wherein said plunger rod further comprises a slot on a distally directed end surface of said plunger rod, wherein said slot is sized to cooperate with said proximally-directed protrusion to rotationally lock said plunger rod to said generally tubular elongated housing when said drive unit is in said energy accumulated state, and wherein said proximally-directed protrusion at said distal end of the generally tubular elongated housing is sized to disengage from said slot when said drive unit is released from said energy accumulated state.

2. The medicament delivery device according to claim 1, wherein the at least one arm is a rigid arm.

3. The medicament delivery device according to claim 2, wherein the at least one arm is axially rigid but radially flexible.

4. The medicament delivery device according to claim 1, wherein the at least one arm is arranged on an inner circumferential surface or on a rim of the tubular element.

5. The medicament delivery device according to claim 1, wherein said tubular element is arranged coaxially outside said plunger rod.

6. The medicament delivery device according to claim 1, wherein said generally tubular elongated housing comprises a proximal housing part and a distal housing part and wherein the plunger rod is rotationally locked to the distal housing part when the drive unit is the energy accumulated state.

7. The medicament delivery device according to claim 1, wherein the medicament delivery device further comprises an activator displaceably arranged in relation to said generally tubular elongated housing and operably arranged to said tubular element such that the displacement of said activator causes said tubular element to be rotated such that the at least one arm disengages from the at least one holding member on said plunger rod whereby the drive unit is released from the energy accumulated state.

8. The medicament delivery device according to claim 7, wherein said activator is slidably arranged along the longitudinal axis of the medicament delivery device between the generally tubular elongated housing and the tubular element.

9. The medicament delivery device according to claim 8, wherein the activator comprises a medicament delivery member guard which is tubular shaped and configured to protrude a certain distance from the proximal end of the generally tubular elongated housing.

10. The medicament delivery device according to claim 9, wherein said tubular element comprises at least one interaction member on an outer circumferential surface of said tubular element, wherein said at least one interaction member is arranged to cooperate with at least one activator element arranged on said activator.

11. The medicament delivery device according to claim 10, wherein said at least one interaction member is arranged inclined in relation to the longitudinal axis of the medicament delivery device.

12. The medicament delivery device according to claim 11, wherein said at least one interaction member comprises an inclined ledge and wherein said at least one activator element comprises a protrusion, wherein the protrusion acts on said inclined ledge to rotate said tubular element when said activator is linearly displaced in relation to said generally tubular elongated housing when the medicament delivery member guard is pressed against a dose delivery site.

13. The medicament delivery device according to claim 12, wherein said activator is arranged with a resilient force member designed to return said activator when said medicament delivery device is removed from the dose delivery site.

14. The medicament delivery device according to claim 13, wherein said tubular element comprises a locking member arranged to interact with said at least one activator element on said activator for locking said activator when returned from moving towards a distal end of the medicament delivery device.

15. The medicament delivery device according to claim 14, wherein said locking member is a flexibly tongue having a stop ledge.

16. The medicament delivery device according to claim 1, wherein the medicament container is arranged with a medicament delivery member though which medicament may be expelled.

17. The medicament delivery device according to claim 1, wherein said medicament delivery device is an injection device.

* * * * *